United States Patent
Wang et al.

(10) Patent No.: US 11,365,435 B2
(45) Date of Patent: Jun. 21, 2022

(54) MULTIPLE-USE RENEWABLE ELECTROCHEMICAL SENSORS BASED ON DIRECT DRAWING OF ENZYMATIC INKS

(71) Applicant: The Regents of the University of California, Oakland, CA (US)

(72) Inventors: Joseph Wang, San Diego, CA (US); Amay Jairaj Bandodkar, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/708,142

(22) Filed: Dec. 9, 2019

(65) Prior Publication Data
US 2020/0115731 A1   Apr. 16, 2020

Related U.S. Application Data

(62) Division of application No. 15/548,735, filed as application No. PCT/US2016/016854 on Feb. 5, 2016, now Pat. No. 10,501,770.
(Continued)

(51) Int. Cl.
*G01N 27/327* (2006.01)
*C12Q 1/00* (2006.01)
(Continued)

(52) U.S. Cl.
CPC .............. *C12Q 1/006* (2013.01); *A61B 5/02* (2013.01); *A61B 5/1486* (2013.01);
(Continued)

(58) Field of Classification Search
CPC ........................................ G01N 27/327–3278
(Continued)

(56) References Cited

U.S. PATENT DOCUMENTS

| | | | | |
|---|---|---|---|---|
| 3,984,000 A | * | 10/1976 | Miller | B65D 75/42 206/531 |
| 5,160,418 A | * | 11/1992 | Mullen | C12Q 1/005 204/403.14 |

(Continued)

FOREIGN PATENT DOCUMENTS

| | | |
|---|---|---|
| WO | 2014070801 A1 | 5/2014 |
| WO | 2014171891 A1 | 10/2014 |

OTHER PUBLICATIONS

Bandodkar et al., "Epidermal tattoo potentiometric sodium sensors with wireless signal transduction for continuous non-invasive sweat monitoring", Biosens. Bioelectron. 2014, vol. 54, pp. 603-609.
(Continued)

*Primary Examiner* — Bach T Dinh
(74) *Attorney, Agent, or Firm* — Perkins Coie LLP

(57) ABSTRACT

Methods, systems, and devices are disclosed for providing a portable enzymatic-ink dispensing system. The system includes an enzymatic-ink including one or more biocompatible binders, one or more biocompatible mediators, an enzyme, an enzyme stabilizer, and a conductive material. The system includes a dispenser including a chamber to hold the enzymatic-ink and an applicator to apply the enzymatic ink dispensed from the chamber onto a target substrate.

15 Claims, 18 Drawing Sheets

Related U.S. Application Data

(60) Provisional application No. 62/112,587, filed on Feb. 5, 2015.

(51) Int. Cl.
      *A61B 5/00*          (2006.01)
      *A61B 5/145*        (2006.01)
      *A61B 5/1486*      (2006.01)
      *A61B 5/02*          (2006.01)

(52) U.S. Cl.
      CPC ........ *A61B 5/14532* (2013.01); *A61B 5/6898* (2013.01); *C12Q 1/001* (2013.01); *G01N 27/3271* (2013.01); *G01N 27/3272* (2013.01)

(58) Field of Classification Search
      USPC ..... 204/403.01–403.15; 205/777.5–778, 792
      See application file for complete search history.

(56) References Cited

U.S. PATENT DOCUMENTS

| | | |
|---|---|---|
| 2003/0023189 A1 | 1/2003 | Kuo |
| 2005/0178674 A1 | 8/2005 | Hyland et al. |
| 2006/0175205 A1* | 8/2006 | Cui ........................ C12Q 1/006 205/777.5 |
| 2007/0007133 A1* | 1/2007 | Mang ..................... C12Q 1/006 204/403.14 |
| 2008/0156662 A1 | 7/2008 | Wu et al. |
| 2008/0210574 A1 | 9/2008 | Boecker |
| 2010/0230284 A1* | 9/2010 | Stephenson ............. B01L 3/502 204/403.01 |
| 2011/0042225 A1* | 2/2011 | Adeloju ................. B82Y 30/00 205/170 |
| 2012/0122197 A1* | 5/2012 | Jospeh ............... G01N 27/3272 435/283.1 |
| 2013/0098775 A1* | 4/2013 | Pei ........................ C12Q 1/006 205/777.5 |
| 2013/0144131 A1 | 6/2013 | Wang et al. |
| 2013/0186755 A1* | 7/2013 | Chu ................... G01N 27/3272 204/403.14 |
| 2014/0209483 A1 | 7/2014 | Sanofi et al. |
| 2015/0198554 A1* | 7/2015 | Cai .................... G01N 27/3272 204/403.02 |

OTHER PUBLICATIONS

Bhattacharyya et al., "Reusable glucose sensing using carbon nanotube-based self-assembly", Nanoscale 2013, 5, 9231.
Cameron et al., "Utilization and Expenditure on Blood Glucose Test Strips in Canada", Can. J. Diabetes 2010, 34, 34.
Ciglanska et al., "Viscometry determination of the kinetic of degradation of iron-gall inks", Acta Chim. Slov. 2012, 5, pp. 126-130.
Combes et al., "Stabilizing Effect of Polyhydriv Alcohols", Acad. Sci. 1990, 613, pp. 559-563.
Dossi et al., "Doped pencil leads for drawing modified electrodes on paper-based electrochemical devices", Electroanal. Chem. 2014, vol. 90, pp. 722-723.
Dossi et al., "Pencil leads doped with electrochemically deposited Ag and AgCl for drawing reference electrodes on paper-based electrochemical devices", Electrochim. Acta 2014, 146, pp. 518-524.
El-Molla, "Synthesis of polyurethane acrylate oligomers as aqueous UV-curable binder for inks of ink jet in textile printing and pigment dyeing", Dyes Pigments 2007, 74, pp. 371-379.
Frazier et al., "Fully-drawn carbon-based chemical sensors on organic and inorganic surfaces", Lab Chip 2014, 14, 4059.
Fukushima et al., "Biodegradation of poly(lactic acid) and its nanocomposites", Polym. Degrad. Stabil. 2009, 94, pp. 1646-1655.
Gao et al., "Directly Writing Resistor, Inductor and Capacitor to Composite Functional Circuits: A Super-Simply Way for Alternative Electronics", PLoS One 2013, 8, e69761.
Han et al., "BioPen: direct writing of functional materials at the point of care", Sci. Rep. 2014, 4, 4872.
Honeychurch et al., "Screen-printed electrochemical sensors for monitoring metal pollutants", Trend. Anal. Chem. 2003, 22, pp. 456-469.
Hu et al., "Preparation and characterization of poly(ethylene glycol)-g-chitosan with water- and organosolubility", Carbohydr. Polym. 2005, 61, pp. 472-479.
International Search Report and Written Opinion for PCT Application No. PCT/US2016/016854, dated Jun. 10, 2016, 9 pages.
Iyer et al., "Enzyme stability and stabilization-Aqueous and non-aqueous environment", Process Biochem. 2008, 43, pp. 1019-1032.
Janigova et al., Thermal degradation of plasticized poly(3-hydroxybutyrate) investigated by DSC), Polym. Degrad. Stabil. 2002, 77, pp. 35-41.
Jia et al., "Electrochemical Tattoo Biosensors for Real-Time Non-invasive Lactate Monitoring in Human Perspiration", Anal. Chem. 2013, vol. 85, pp. 6553-6560.
Jia et al., "Wearable textile biofuel cells for powering electronics", J. Mater. Chem. A 2014, 2, p. 18184.
Karter et al., "Out-of-Pocket Costs and Diabetes Preventive Services", Diabetes Care 2003, 26, pp. 2294-2299.
Karter et al., "Self-Monitoring of Blood Glucose: Language and financial barriers in a managed care polulation with diabetes", Diabetes Care 2000, 23, pp. 477-483.
Kiani et al., "Reusable and robust high sensitive non-enzymatic glucose sensor based on Ni(OH)2 nanoparticles", Anal. Chim. Acta 2014, 839, pp. 26-33.
Martinez et al., "Diagnostics for the Developing World: Microfluidic Paper-Based Analytical Devices", Anal. Chem. 2010, vol. 82, pp. 3-10.
Mirica et al., "Mechanical Drawing of Gas Sensors on Paper", Angew. Chem. 2012, 43, 10898; Angew. Chern. Int. Ed. 2012, 51, pp. 10740-10745.
Mirica et al., "Rapid prototyping of carbon-based chemiresistive gas sensor on paper", Proc. Natl. Acad. Sci. U.S.A. 2013, 110, pp. E3265-E3270.
Mulchandani et al., "Biosensors for direct determination of organophosphate pesticides", Biosens. Bioelectron. 2001, 16, pp. 225-230.
Newman et al., "Home blood glucose biosensors: a commercial perspective", Biosens. Bioelectron., 2005, vol. 20, p. 2435-2453.
Özcan et al., "Non-enzymatic glucose biosensor based on overoxidized polypyrrole nanofiber electrode modified with cobalt(II) phthalocyanine tetrasulfonate", Biosens. Bioelectron. 2008, 24, pp. 512-517.
Ozsoz et al., "Electrochemical Genosensor Based on Colloidal Gold Nanoparticles for the Detection of Factor V Leiden Mutation Using Disposable Pencil Graphite Electrodes", Anal. Chem. 2003, 75, pp. 2181-2187.
Pielichowski et al., "Differential Scanning Calorimetry Studies on Poly(ethylene Glycol) with Different Molecular Weights for Thermal Energy Storage Materials", Polym. Adv. Technol. 2002, 13, pp. 690-696.
Poorahong et al., "Amperometric sensor for detection of bisphenol A using a pencil graphite electrode modified with polyaniline nanorods and multiwalled carbon nanotubes", Microchim. Acta 2012, 176, pp. 91-99.
Russo et al., "Pen-on-Paper Flexible Electronics", Adv. Mat. 2011,23, pp. 3426-3430.
Taghizadeh et al., "Calculation of the rate constant for the ultrasonic degradation of aqueous solutions of polyvinyl alcohol by viscometry", Ultrason. Sonochem. 2003, 10, pp. 309-313.
Veronese et al., "PEGylation, successful approach to drug delivery", Drug Discov. Today 2005, 10, pp. 1451-1458.
Vestergaard et al., "An electrochemical approach for detecting copper-chelating properties of flavonoids using disposable pencil graphite electrodes: Possible implications in copper-mediated illnesses", Anal. Chim. Acta 2005, 538, pp. 273-281.
Wang et al., "Amplified label-free electrical detection of DNA hybridization", Analyst 2002, 127, pp. 383-386.
Wang et al., "Capillary electrophoresis microchips with thick-film amperometric detectors: separation and detection of phenolic compounds", Anal. Chim. Acta 2000, 416, pp. 9-14.

(56) References Cited

OTHER PUBLICATIONS

Wang et al., "Renewable pencil electrodes for highly sensitive stripping potentiometric measurements of DNA and RNA", Analyst 2000, 125, pp. 5-7.
Wang, "Electrochemical biosensors: Towards point-of-care cancer diagnostics", Biosens. Bioelectron. 2006, vol. 21, pp. 1887-1892.
Wang, "Electrochemical glucose biosensors", Chem. Rev. 2008, vol. 108, pp. 814-825.
Wang et al. "Amperometric Biosensor for Phenols Based on a Tyrosinase-Graphite-Epoxy Biocomposite" Analyst, Mar. 1994, vol. 119. 455-458.
Wisniewski et al., "Characterization of implantable biosensor membrane biofouling", Anal. Chem. 2000, 366, pp. 611-621.
Wu et al., "Direct Inkjet Printing of Silver Nitrate/Poly(N-vunyl-2-pyrrolidone) Inks to Fabricate Silver Conductive Lines", J. Phys. Chem. C 2010, 114, pp. 4659-4662.
Yager et al., "Point-of-Care Diagnostics for Global Health", Annu. Rev. Biomed. Eng. 2008, 10, pp. 107-144.
Ye et al., "Influence of additives on the thermostability of glucose oxidase", Enzyme Microb. Tech. 1988, 10, pp. 498-502.
Zanni et al., "Graphite Nanoplatelets and Caenorhabditis elegans: Insights from an in Vivo Model", Nano Lett. 2012, 12, pp. 2740-2744.

\* cited by examiner

MULTIPLE-USE RENEWABLE ELECTROCHEMICAL SENSORS BASED ON DIRECT DRAWING OF ENZYMATIC INKS

CROSS-REFERENCE TO RELATED APPLICATIONS

This patent document is a divisional of U.S. patent application Ser. No. 15/548,735 entitled "MULTIPLE-USE RENEWABLE ELECTROCHEMICAL SENSORS BASED ON DIRECT DRAWING OF ENZYMATIC INKS" filed on Aug. 3, 2017, which is National Phase Applications of PCT Application No. PCT/US2016/016854 entitled "MULTIPLE-USE RENEWABLE ELECTROCHEMICAL SENSORS BASED ON DIRECT DRAWING OF ENZYMATIC INKS" FILED ON Feb. 5, 2016 which claims the benefit of priority of U.S. Provisional Patent Application No. 62/112,587 entitled "MULTIPLE-USE RENEWABLE ELECTROCHEMICAL SENSORS BASED ON DIRECT DRAWING OF ENZYMATIC INKS" filed on Feb. 5, 2015. The entire contents of the above patent applications is incorporated by reference as part of this patent document.

TECHNICAL FIELD

This patent document relates to electrochemical sensors.

BACKGROUND

Electrochemical sensors are the gold standard in the field of biosensors. This is especially true in case of the billion dollar finger-stick blood glucose diagnostics market. Self-monitoring of blood glucose is a billion dollar industry that relies on single-use disposable strips. Hand-held electrochemical enzymatic sensors have been in the diabetes market for several decades and are considered as a bench-mark in the field of biosensors. These sensors rely on enzyme-coated sensor strips that produce a signal proportional to the concentration of the concerned chemical species. The concentration is then displayed on a hand-held analyzer. Majority of these sensors employ single-use sensor strips.

According to WHO's latest statistics almost 400 million people have been affected by diabetes globally. Blood glucose monitoring is extremely critical for diabetics and the hand-held glucose meters play a central role in diabetes management. Since blood glucose must be measured multiple times daily, the use of single-use glucose strips adds considerable financial burden on the patients. Multiple-use sensor strips can address this issue.

SUMMARY

Disclosed are methods, systems, and devices that provides for repeated blood glucose monitoring using a single sensor strip. The described methods, systems, and devices use enzymatic ink loaded in roller pens ("enzymatic pen") to draw active enzyme layer on a reusable strip for repeated blood glucose monitoring in conjugation with a hand-held electronic display unit. Once the test is done, unlike a single use glucose strips, the user simply wipes the enzyme layer off the sensor surface using a moist cotton swab/napkin, for example. The active enzyme layer can then be re-drawn using the 'enzymatic pen' for the next blood test. Wiping or erasing the sensor surface with moist cotton swab, for example, can substantially completely remove the enzyme layer to regenerate the bare sensor surface and thus the same strip can be used multiple times with the help of the 'enzymatic ink' without the need to use a fresh strip. By using the same sensor strip for repeated diagnosis, the overall cost involved in each blood testing can be reduced.

The disclosed methods, systems, and devices can be implemented to provide for detection of glucose levels in buffer as well as in undiluted human blood sample. Also, the described methods, systems, and devices can provide techniques of using enzymatic inks for fabricating sensors and biofuel cells directly drawn on diverse substrates (for example, leaves, cellphone, walls, paper etc.). However, the approach can be extended to various diverse applications that use reusable electrochemical sensors. The transfer of the ink to a substrate is not limited to roller pen and other mediums, for example but not limited to squeeze tubes, syringes and stamps can also be used.

The present document pertains to technology for the development of reusable sensor strips for electrochemical detection of blood glucose by using 'do-it yourself' "enzymatic pens". The disclosed technology is not limited to detection of blood glucose and can be easily modified to obtain reusable sensor strips for other chemical species. The disclosed technology can be also used to draw electrochemical sensors and biofuel cells on various unconventional surfaces. Currently, electrochemical sensors and biofuel cells are fabricated on conventional substrates, for example, ceramic, plastics, paper etc. using expensive and sophisticated techniques like lithography, screen printing, ink-jet etc. The disclosed technology provides for a simple inexpensive strategy for on-site direct incorporation of sensors on unconventional substrates for diverse physiological and environmental monitoring. The disclosed technology provide for the use of "enzymatic pens" that can be used to directly draw electrochemical sensors and biofuel cells on diverse surfaces, for example, but not limited to cellphone cover, leaves, human skin, paper etc. By using the "enzymatic pens" users can simply draw electrochemical devices directly on a rich variety of surfaces for various applications.

The present document also discloses a reusable sensor integrated onto a custom-built smartphone case for electrochemical detection of blood glucose by using "enzymatic pellet based stylus" that is housed in the custom-built smartphone case. While blood glucose level detection is used as an example, the technology is not limited to blood glucose and can be easily modified to obtain reusable sensor strips for other chemical species. Similarly, in other embodiments, not limited to smartphones, renewable enzymatic sensors can be similarly integrated on other consumer electronics and computing devices, for example, tablets, laptops or other consumer electronics.

In some disclosed embodiments, the biosensors may be enabled by enzymatic ink loaded in roller pens, e.g., enzymatic pens, that can draw active enzyme layers, thus allowing for easy renewal of sensing components and repeated use of substrates. An example application would be blood glucose monitoring in conjunction with a hand-held electronic unit with display, where the glucose strip becomes reusable, or the enzymatic sensors can be drawn/erased at will over electrodes on the unit.

The disclosed technology can be used to detect glucose levels in buffer as well as in undiluted human blood sample. The transfer of the ink to a substrate is not limited to roller pen and other mediums, for example but not limited to squeeze tubes, syringes and stamps can also be used in connection to diverse surfaces.

In some disclosed embodiments, a portable apparatus includes a dispenser, a case and an electrochemical sensor.

The dispenser has volume to hold and dispense one or more individually dispensable pellets made up of an enzyme compound. The case includes a mechanism using which the dispenser can be attached to the case. The electrochemical sensor is attached to the case and having a reference electrode, a working electrode and a counter electrode arranged to provide a flat surface for application of the enzyme compound and a chemical for sensing and to produce an electrical signal resulting from the sensing.

These, and other, features are described in greater detail in the present document.

BRIEF DESCRIPTION OF THE DRAWINGS

FIG. 2E shows a phone after wiping off a sensor ready for next test by drawing a fresh sensor using a "enzymatic pen".

DETAILED DESCRIPTION

Figure 1:
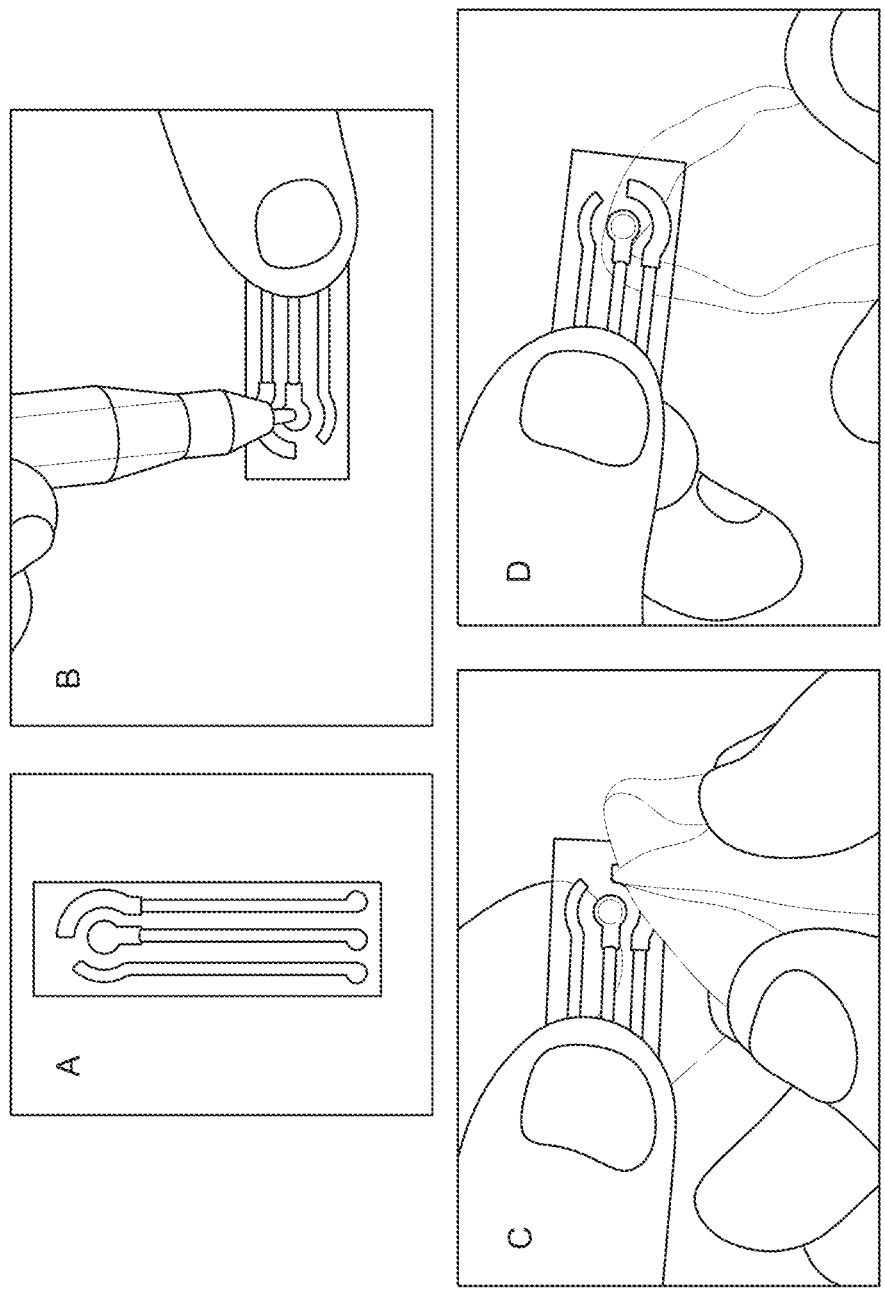
FIG. 1 shows using a re-usable sensor strip or pattern. Image A shows an exemplary bare sensor strip or pattern. Image B shows drawing an active enzyme layer using the "enzymatic pen". Image C shows wiping off the enzyme layer using a moist cotton swab after completion of the test. Image D shows regeneration of the sensor strip for its next use.

The disclosed technology can provide for a 'Do-it-Yourself' (DIY) blood chemical monitoring directly on cellphones or smartphones using roller pens filled with enzymatic ink ("enzymatic pen") as an alternative to the single-use hand-held blood analyzers. When performing the blood test, the user draws a fresh active enzyme layer on to the sensor surface integrated with a pre-defined sensor pattern on the cellphone or smartphone. The sensor pattern with the drawn active enzyme later then detects the desired chemical present in the blood and displays the information (e.g., concentration) directly on the cellphone or smartphone to the user. The information can also be transmitted from the cellphone or smartphone to the cloud (e.g., for storage) or to the user's physician/healthcare provider. The sensor electronics (e.g., for detection, data recording, display and transmission) can be embedded within the cellphone or smartphone itself or as an attached device. Furthermore, the enzymatic ink can also be filled within specially designed stylus that can work also as an enzymatic pen in addition to its usual use of writing/drawing/navigating on the cellphone or smartphone. The stylus can be housed within the cellphone body. Once the test is done, unlike the presently available single use blood monitoring strips, the user simply wipes the enzyme layer off the sensor surface using a moist cotton swab/napkin. The active enzyme layer can then be re-drawn on the same sensor pattern using the 'enzymatic pen' for the next blood test. These sensors are referred to as DIY sensors since the users make the sensor by themselves in a highly reproducible manner. Multiple enzyme inks can be loaded within a single pen, analogous to multi-color pens, for multi-analyte detection.

The disclosed technology can be used to integrate an inexpensive renewable blood chemical sensor within a cellphone or smartphone. The renewable sensor and the ubiquitous presence of cellphones or smartphone provide for a cost-effective and easy to use solution. The disclosed technology provides for enzymatic ink-based pens that can be used to draw enzymatic sensors directly onto cell-phones for "on-demand" blood chemical analysis. Such sensors can be customized to detect blood analytes like, but not limited to, glucose, lactate, alcohol, electrolytes.

The disclosed technology can be used to synthesize customized enzymatic inks that can be loaded in roller pens for direct writing of renewable enzymatic sensors directly onto the integrated predefined sensor pattern on the cellphones or smartphones for customized point-of-care blood chemical diagnosis. The disclosed technology deals with drawing renewable enzymatic sensors on cellphones or smartphones for decentralized blood chemical analysis. The disclosed technology involves drawing fresh enzyme layer on to the sensor surface pre-defined on the cellphones or smartphones for each blood test using enzymatic pen. Since the renewable sensor is drawn directly onto the cellphone or smartphone, the users do not need to carry the sensor strips and the associated sensor electronics with them. The enzymatic ink can be filled within specially designed stylus that will work also as an enzymatic pen in addition to its usual use of writing/drawing/navigating on the cellphone or smartphone. Multiple enzyme inks can be loaded within a single pen, analogous to multi-color pens, for multi-analyte detection.

FIG. 1 shows using a re-usable sensor strip or pattern. Image A shows an exemplary bare sensor strip or pattern. The exemplary sensor pattern shows three electrodes but in some implementations, only two electrodes can be used. For example, when used as a potentiometer to detect a potential difference, two electrodes including a working electrode and an auxiliary electrode may be sufficient. When detecting an amperometric or voltammetric response, three electrodes including a working electrode, an auxiliary electrode and a reference electrode can be used. The reference electrode can assist in maintaining constant potential while passing current to counter redox events at the working electrode. Image B shows drawing an active enzyme layer using the "enzymatic pen". When the enzyme layer customized to detect a desired analyte or target is applied, the sensor can be used to perform the desired detection. Image C shows wiping off the enzyme layer using a moist cotton swab after completion of the test. By wiping off the enzyme layer, the sensor pattern with the electrodes are ready to be reused. Image D shows regeneration of the sensor strip for its next use.

Techniques, systems and devices are described for providing a single sensor strip that can be renewed after each use. In one aspect, an enzymatic ink-based pens can be used for fabricating reusable glucose sensors. The concept is not limited to glucose (diabetes) sensing and can be easily extended to other analytes by using different enzymes.

The present document describes the technique to synthesize customized enzymatic inks that can be loaded in roller pens for direct writing of enzymatic electrodes for sensing and energy applications. An application of these inks is in the development of re-usable sensor strips for blood glucose monitoring as well as for other substrates of enzymatic reactions generating electroactive product. Reusable glucose sensors that use the same reagent layer multiple times can be limited by the memory and fouling effect from previous measurements and variation of sensor response due to leaching of the enzyme over repeated use. The described renewable sensor strip can provide for a substantially complete regeneration of the active enzyme layer after every use, which can avoid the memory and fouling effects of reusable glucose sensors that use the same reagent layer multiple times. The substantially complete regeneration of the active enzyme layer can be achieved by substantially complete removal of the old enzyme-based ink by wiping off the layer using a moist cotton swab followed by re-drawing the layer using the customized enzymatic pen. Using the "enzymatic pen" to draw the enzyme layer is extremely easy. It is similar to using any commercial roller pens. Such enzymatic pens are not limited to re-usable glucose strips and can be easily extended to developing other re-usable enzyme-based sensor strips and also enzymatic sensors and biofuel cells on various substrates not limited to cellphones, leaves, human skin, wall, paper.

The system can include customized enzymatic ink-filled roller pen ("enzymatic pen"), a "sensor pattern" or a screen printed "sensor strip" involving a three electrode contingent (and optionally an electrochemical analyzer) predefined onto the cellphone or smartphone. The enzymatic ink can be prepared by mixing biocompatible binders like, but not limited to, polyethylene glycol and chitosan. Biocompatible mediators like methylene green, prussian blue etc. are also added to the ink. Depending on the target analyte, the concerned enzyme is mixed in the ink. In the present case, glucose oxidase enzyme can be used for detecting glucose levels. Polyhydric alcohol (xylitol, ethylene glycol, glycerol, erythritol or sorbitol) can be added to the enzymatic ink as enzyme stabilizer. Graphite can be dispersed within the ink for making it conductive. All the components are thoroughly mixed using a bath sonicator followed by filling the ink into commercially-available roller pens (in the present case GELLY ROLL® pens were used) to develop the "enzymatic pen". The ink can be filled in a specially designed stylus that will work also as an enzymatic pen in addition to its usual use of writing/drawing/navigating on the cellphone or smartphone. The loaded stylus, housed within the cellphone or smartphone body, can be used for hundreds of tests over several months.

The enzymatic pen can then be used to draw the active enzyme layer on the sensor patterned directly onto the cellphone or smartphone body. This can be achieved by drawing directly or with the help of a stencil on the pre-defined region marked on the sensor strip followed by air drying for a short time (1-3 min). The sensor can now be used for measuring the desired analyte in the sample by coupling it to the electrochemical analyzer. During operation, the analyzer applies a constant potential and measures the current produced. The current generated is proportional to the concentration of the analyte. The analyzer then displays the concentration of the analyte present in the sample (e.g. blood). The sensor electronics (e.g., for detection, data recording, display and transmission) can be embedded within the cellphone or smartphone itself.

Upon completion of the test, the user can remove the enzyme layer from sensor strip by simply wiping it off using a moist cotton swab. Fresh active enzyme layer can now be redrawn over the pre-defined sensor pattern or strip using the enzymatic pen for the next test. FIG. 1 illustrates the entire process in detail for a sensor pattern developed on a flexible plastic substrate as for developing renewable sensor directly onto cellphones using enzymatic pens. Such a pattern can be easily developed on the cellphone or smartphone body using fabrication techniques commonly used for making cellphone or smartphone electronic parts. The enzymatic pen can be used for developing renewable enzymatic sensors for other analytes by changing the enzyme and other reagents in the enzymatic ink.

Figure 2:
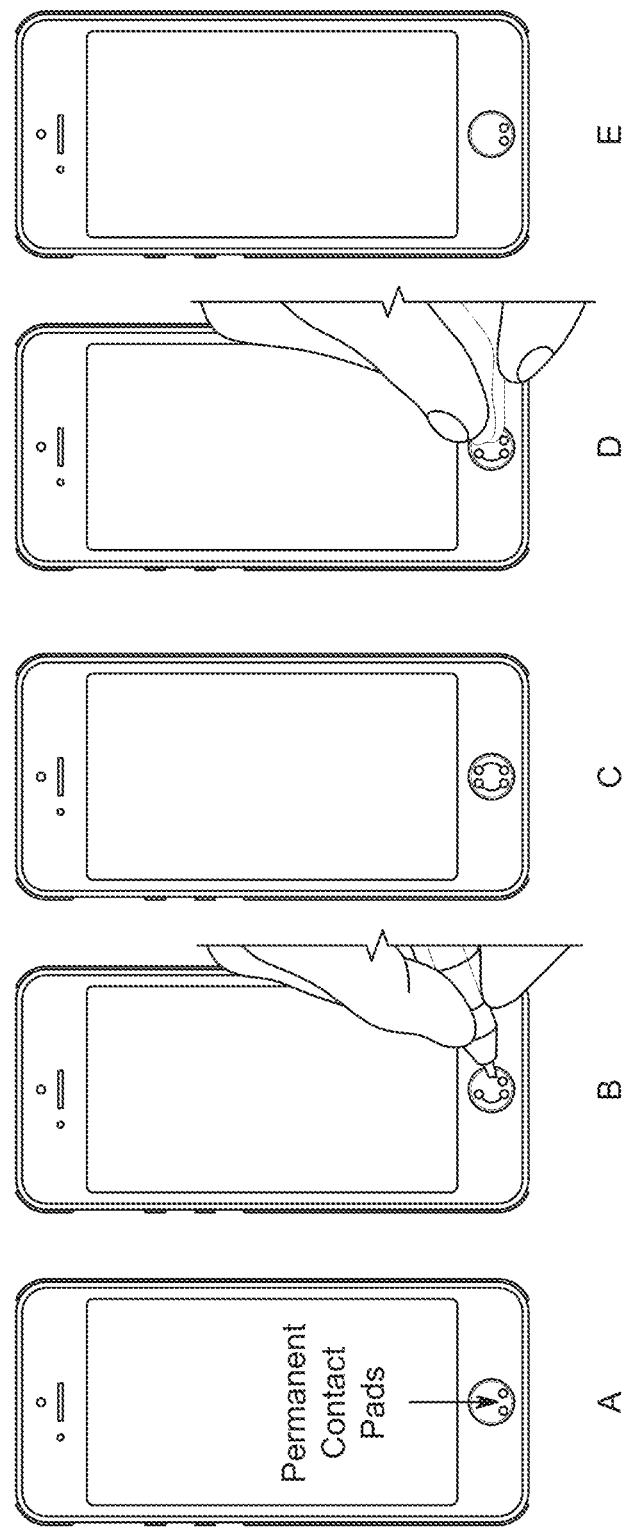
FIG. 2 is a series of image showing a possibility of using an "enzymatic pen" for obtaining drawable sensor directly on a smartphone for personalized health monitoring. Image A is an image of a smartphone with integrated permanent contact pads for sensor. Image B shows drawing of a sensor over the contact pads of the phone. Image C shows a drawable sensor on phone for personalized diagnostics. Image D shows wiping off the sensor using a cotton swab.

Exemplary data obtained are shown below:

FIG. 2 is a series of images showing a possibility of using an "enzymatic pen" for obtaining drawable sensor directly on a smartphone for personalized health monitoring. Image A is an image of a smartphone with integrated permanent contact pads for sensor. Image B is a drawing of a sensor over the contact pads of the phone. Image C is a drawable sensor on phone for personalized diagnostics. Image D is a wiping off the sensor using a cotton swab. Image E is a phone after wipping off the sensor ready for next test by the drawing a fresh sensor using the "enzymatic pen".

Figure 3:
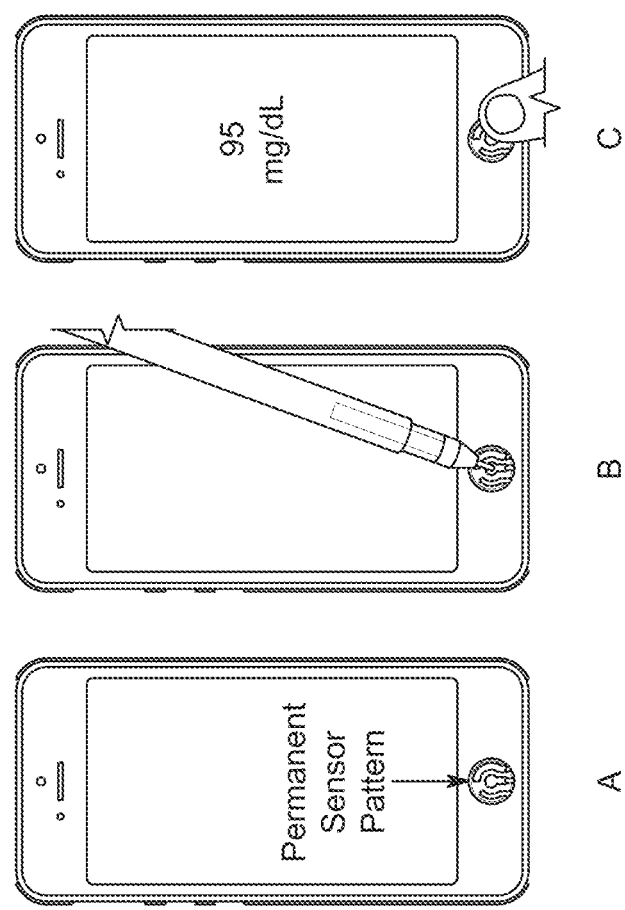
FIG. 3 is a series of images showing the possibility of using the "enzymatic pen" for obtaining drawable sensor directly on a smartphone for personalized health monitoring. (A) Image of a smartphone with integrated permanent sensor pattern. (B) Drawing of a sensor over the pre-defined sensor pattern. (C) Blood analysis and display of the chemical concentration directly on the cellphone.

FIG. 3 is a series of images showing another example of using the "enzymatic pen" for obtaining drawable sensor directly on a smartphone for personalized health monitoring. Image (A) shows a smartphone with integrated permanent sensor pattern. Image (B) shows drawing of a sensor over the pre-defined sensor pattern. Image (C) shows blood analysis and display of the chemical concentration directly on the cellphone.

Figure 4:
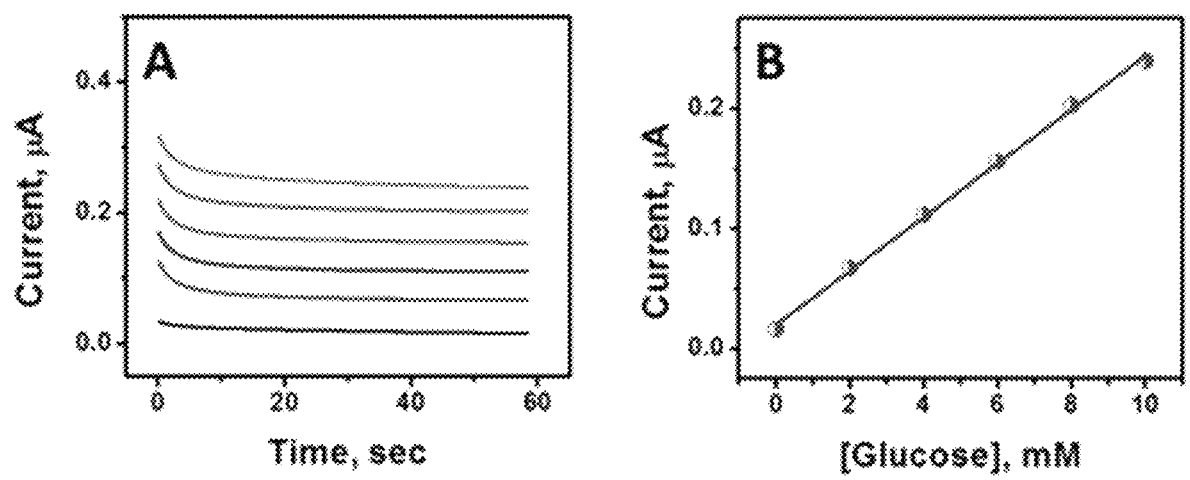
FIG. 4 shows in panel A, amperometric response obtained from a reusable glucose sensor strip fabricated by drawing the enzymatic layer using the "enzymatic pen" on the sensor strip for increasing glucose concentrations in buffer. Panel B shows a calibration plot for the sensor.

FIG. 4 shows in panel A, an exemplary amperometric response obtained from a reusable glucose sensor strip fabricated by drawing the enzymatic layer using the "enzymatic pen" on the sensor strip for increasing glucose concentrations in buffer. FIG. 4 also shows in panel B, a calibration plot for the sensor.

Figure 5:
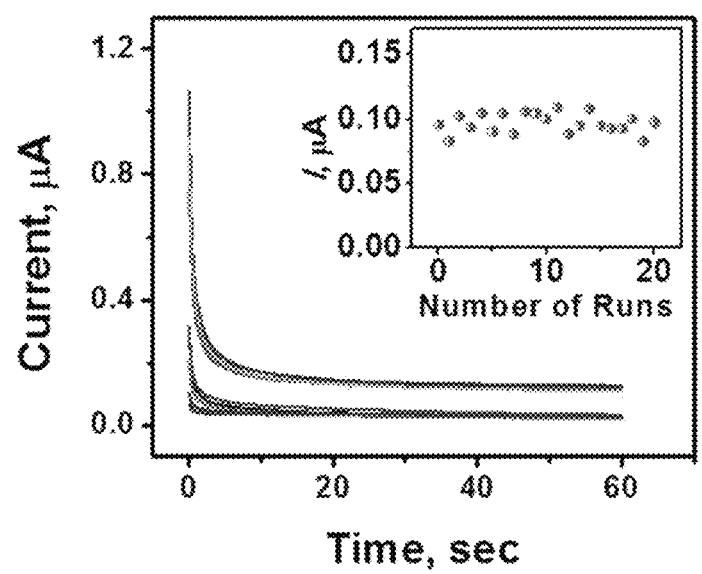
FIG. 5 shows an exemplary amperometric response obtained from a single renewable glucose sensor drawn on a flexible sensor strip, as a proof-of-principle for direct detection of blood analytes onto a cellphone using the "enzymatic pen" for 0 mM and 2 mM glucose in buffer for 20 repetitive sensor drawings. Inset shows an exemplary response for each of the 20 reuse cycles.

FIG. 5 shows amperometric response obtained from a single renewable glucose sensor drawn on a flexible sensor strip, as a proof-of-principle for direct detection of blood analytes onto a cellphone using the "enzymatic pen" for 0 mM and 2 mM glucose in buffer for 20 repetitive sensor drawings. Inset shows response for each of the 20 reuse cycles.

Figure 6:
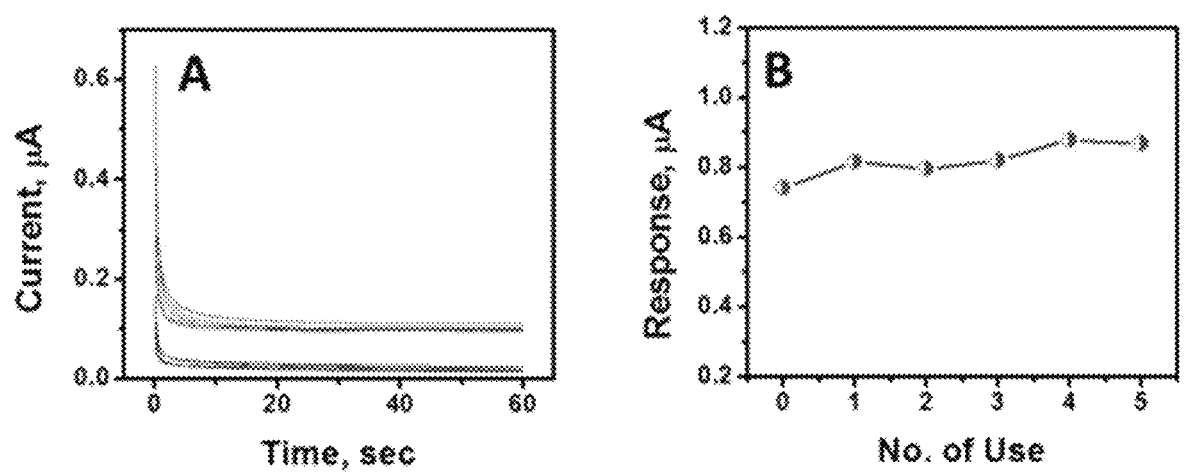
FIG. 6 shows a response obtained from a reusable single sensor strip for 0 mM and 2 mM glucose in buffer for 5 repetitive sensor drawings.

FIG. 6 shows a response obtained from a reusable single sensor strip for 0 mM and 2 mM glucose in buffer for 5 repetitive sensor drawings. Panel A shows the current vs. time relationship, and panel B shows the current vs. number of use relationship.

Figure 7:
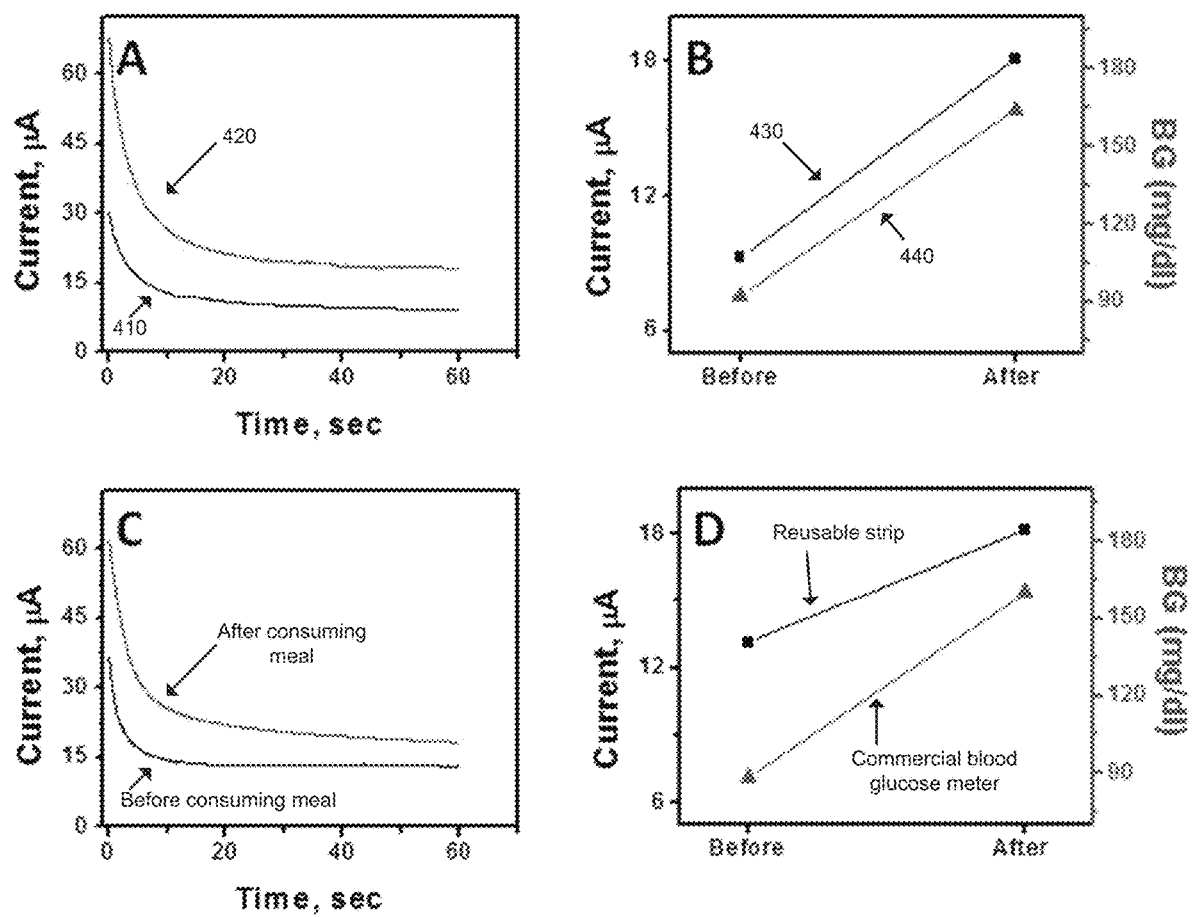
FIG. 7 shows in panel A, an amperogram obtained for enzyme-drawn sensor strip before (410) and after (420) consuming meal. Panel B shows correlation of the data obtained from the reusable strip (430) with commercial blood glucose meter (440). Panels C and D show an experiment similar to FIG. 4 performed using a different reusable sensor strip.

FIG. 7 shows in panel A an amperogram obtained for enzyme-drawn sensor strip before (410) and after (420) consuming meal. Panel B shows correlation of the data obtained from the reusable strip (430) with commercial blood glucose meter (440). Panels C and D represent experimental data similar to FIG. 6 performed using a different reusable sensor strip.

Biocompatible Enzymatic Roller Pens for Direct Writing of Biocatalytic Materials: "Do-it-Yourself" Electrochemical Biosensors The development of enzymatic ink-based roller pens for direct drawing of biocatalytic sensors, in general, and for realizing renewable glucose sensor strips, in particular, is described. The resulting enzymatic-ink pen allows facile fabrication of high-quality inexpensive electrochemical biosensors of any design by the user on a wide variety of surfaces having complex textures with minimal user training. This technique thus enables the end-user with the ability of "on-demand" and "on-site" designing and fabricating of biocatalytic sensors to suit their immediate requirement. The resulting devices are thus referred to "Do-it-Yourself" sensors. The bioactive pens produce highly reproducible biocatalytic traces with minimal edge roughness. The composition of the new enzymatic inks has been optimized for ensuring good biocatalytic activity, electrical conductivity, biocompatibility, reproducible writing and surface adherence. The resulting inks have been characterized using spectroscopic, viscometric, electrochemical, thermal and microscopic techniques. Applicability to renewable blood glucose testing, epidermal glucose monitoring and on-leaf phenol detection are demonstrated in connection to glucose-oxidase and tyrosinase based carbon inks. The 'Do-it-Yourself' renewable glucose sensor strips offer a 'fresh', reproducible, low-cost biocatalytic sensor surface for each blood test. The ability to directly draw biocatalytic conducting traces even on unconventional surfaces opens up new avenues in various sensing applications in low-resource settings and holds great promise for diverse healthcare, environmental and defense domains.

Introduction

Decentralized monitoring of vital parameters for personalized health monitoring has been the Holy Grail for affordable healthcare. This is especially true in the case of diabetes. According to the International Diabetes Federation, over 400 million people have been affected globally by Diabetes till 2013, and this number is expected to reach a staggering 600 million by 2035. Regular self-monitoring of blood glucose (SMBG) performed by hand-held glucose meters is considered the cornerstone for effective diabetes management. Despite the advantages of glucometers (ease of use, availability), these devices rely on single-use sensor strips, and the stinging cost involved in each SMBG test puts a considerable financial burden on the Diabetic community, especially the lower income section. Studies have proved that higher out-of-pocket costs for glucometer strips have led to lower frequency of SMBG tests, and hence to suboptimal diabetes management. Accordingly, there is a pressing need for reducing the cost per SMBG test for diabetes testing in low-resource settings. Several researchers have made efforts to address this issue by developing multiple-use glucose sensors. However, memory-effect due to previous tests, biofouling of the sensor surface and leaching of reagents from the sensor due to repeated use compromise the sensor response and limit the use of such reusable sensors. A renewable sensor that completely regenerates its enzymatic surface for every new blood test should address these limitations while keeping the expense of glucose testing low.

The present article describes a technique that addresses these concerns by utilizing enzymatic ink-based roller pens to draw "fresh" and reproducible active glucose-oxidase (GOx) electrode layers on the same sensor strip for multiple blood glucose tests. The new method relies on an enzymatic pen containing an inexpensive biocatalytic ink that can be used to draw approximately 500 high-fidelity renewable sensor strips. Such user-drawn renewable "Do-it-Yourself" (DIY) biosensors are thus expected to lower the cost incurred for glucose monitoring without compromising the sensor performance compared to existing single-use test strips. The new direct enzyme writing concept has immense promise beyond low-cost diabetes management, as it offers the creation of variety of poor-resource biocatalytic sensors for healthcare and other applications.

Pencil-based sensors, based primarily on graphite leads, have been used for the development of low cost electrochemical and chemresistive paper diagnostics. However, the development of pencil-based biosensors requires additional electrode functionalization steps, including enzyme immobilization. Execution of such steps mandates technical expertise and hence such sensors cannot be prepared by common untrained users. Furthermore, no work on incorporating such pencil-drawn sensors within unconventional substrates has been conducted. Recent efforts have led to the introduction of silver and liquid metal ink-based roller pens to directly draw interconnects and simple electrical circuits for paper electronics. Han et al. recently demonstrated a 'BioPen' for direct drawing of optical DNA sensors. However, direct writing of biocatalytic materials or one-step drawing of enzymatic electrodes (without additional sensor modification steps) has not been reported.

The present work also aims at filling the above gaps by utilizing the enzymatic ink-based roller pens to directly draw uniform undistorted biocatalytic sensors with minimal defects on conventional flat surfaces as well as well-defined devices on unconventional surfaces having complex texture (e.g. human skin, plant leaves) for diverse healthcare, environmental and security applications. Such one-step fabrication of biocatalytic sensors by the enzymatic bioactive roller-ball pens obviates the need for separate, time-consuming enzyme immobilization steps. Such capabilities are realized by tailoring the ink composition for ensuring high biocatalytic activity, electrical conductivity, reproducible writing and surface adherence. The resulting easy-to-prepare enzymatic pens offer unprecedented latitude to the user to develop "on-demand" DIY biocatalytic sensors of any shape on a variety of surfaces and to camouflage them within their surroundings. Such freedom cannot be offered by pre-fabricated sensors. The enzymatic pen-based DIY sensors thus hold superiority over pre-fabricated sensors in above mentioned scenarios, since the end-user has complete liberty to design and incorporate the sensors within complex surfaces based on the immediate requirements. This attribute makes the new DIY biosensors particularly attractive in the defense and environmental sectors. The following sections discuss in detail the synthesis, optimization, characterization and applications of the enzymatic ink-based roller pens for such diverse biosensing applications.

Experimental Section: Materials and Enzymatic Ink Synthesis

Polyethylene glycol (PEG), Chitosan (CHIT), xylitol, methylene green (MG), Glucose oxidase (GOx) from *Aspergillus niger*, Type X-S (EC 1.1.3.4), tyrosinase (Tyr) from mushroom (EC 1.14.18.1), D (+)-glucose, p-chlorophenol, catechol were procured from Sigma Aldrich (St. Louis, Mo.). Graphite powder (synthetic microcrystals grade APS, 2-15 μm, 99.999%) was obtained from Alfa Aesar (Ward Hill, Mass.), and used as received. All solutions were prepared in deionized water.

The enzymatic ink was prepared by adding each of its individual constituents and sonicating for 30 min. Initial synthesis step involved thorough mixing of 2:1 v/v of PEG (60 wt % in water) and CHIT (1 wt % in 0.1M acetic acid). Subsequently, 2 M xylitol solution was prepared in the above PEG/CHIT mixture. For preparing the GOx-based ink, 0.1 wt % MG was then added. This was followed by adding 30 wt % graphite powder. Finally, 1 wt % of enzyme (Tyr or GOx) was added to the ink. We refer to the enzymatic ink with GOx as GOx Ink and with Tyr as Tyr Ink. Bare graphite ink (Gr Ink) was also prepared (without the enzyme and mediator) for realizing the counter/reference electrodes. The enzymatic inks were kept at 4° C. overnight before use. Thereafter, the inks were gently centrifuged using a benchtop centrifuge for 1 min to separate undispersed graphite particles. The supernatant was then filled in roller pens (Sakura Gelly Roller® pens, Japan) containing an 8 cm long ink reservoir. Prior to filling of the ink, the pens were thoroughly cleansed several times by acetone and then finally with de-ionized water.

Screen printed electrodes were prepared using an MPM-SPM semi-automatic screen printer (Speedline Technologies, Franklin, Mass.) using a previously described fabrication protocol. Electrochemical characterization was performed at room temperature leveraging a CH Instruments (Austin, Tex.) model 630C electrochemical analyzer. Fourier Transform Infrared Spectroscopy (FT-IR) was performed using a PerkinElmer Spectrum Two FT-IR Spectometer (Waltham, Mass.). Differential Scanning calorimetry (DSC) and Thermogravimetric Analysis (TGA) were performed using a PerkinElmer PYRIS Diamond DSC (Waltham, Mass.) and PerkinElmer Pyris 1 TGA Thermogravimetric Analyzer (Waltham, Mass.), respectively.

Drawing of Do-it-Yourself Enzymatic Sensors

In the present work, two-electrode system has been used for detection of analytes. The working electrode consists of enzymatic electrode drawn using the enzymatic ink-filled roller pen while the counter/reference electrode is realized by using Gr Ink. Reproducible DIY sensors can be achieved by using templates of defined electrode area and shape. Upon drawing the sensor, the ink can be cured at room temperature (RT) for 30 min or at 50° C. for 5 min. The sensor can then be interfaced with an electrochemical analyzer for detecting the target analyte.

Characterization of Enzymatic Inks

Detailed characterization of the inks was performed using thermal, optical, microscopic, capillary viscometric and electrochemical techniques. The ability of the GOx Ink to electrochemically detect glucose was studied by drawing the enzymatic working electrode (5 mm×2 mm) on alumina substrate containing the screen printed Ag/AgCl reference electrode and bare carbon counter electrode. The sensor was subjected to increasing glucose concentrations in 0-10 mM range. The detection was carried out using amperometric technique at 0.4V with a 1 min incubation time. The stabilizing effect of xylitol was studied by analyzing sensors drawn using two types of enzymatic inks, one containing GOx but no xylitol (No-Xyl GOx Ink) and GOx Ink. The stability study was carried out over a three week period and an average response obtained from three different sensors drawn using each of the two inks was studied on every alternate day by exposing the sensors to a 2 mM glucose solution. At the end of the study (Day 21), the GOx Ink-based sensor was again tested over the 0-10 mM range for comparison with sensor response on Day 0.

FT-IR spectroscopy of GOx Ink was carried out on the same day of synthesis (Day 0) and then after storing the ink for one week (Day 7) at RT as well when stored at 4° C. Thermal studies consisted of using DSC for analyzing the GOx Ink on Day 0 and Day 7. On each day two types of samples were tested—(i) GOx Ink and (ii) GOx Ink cured at 50° C. for 5 min. During the DSC study, each sample was held at 20° C. for 1 min followed by heating it from 20° C. to 100° C. at a heating rate of 10° C./min. The sample temperature was held constant at 100° C. for 1 min followed by cooling to 20° C. at a cooling rate of 10° C./min. The effect of heating on the mass change of the GOx Ink was studied using TGA by heating the sample from 20° C. to 100° C. at a heating rate of 10° C./min and then cooling to 20° C. at the same rate. SEM and optical images of traces drawn using bare graphite ink without xylitol (No-Xyl Gr Ink), No-Xyl GOx Ink and GOx Ink on printer paper were obtained to analyze the effect of GOx and xylitol on the morphological variations of the ink traces. The effect of repeated bending stress on the conductivity of traces drawn using Gr Ink and GOx Ink was also examined using a multi-meter. For this study, 10 mm×3 mm traces were drawn on printer paper and the resistance measured after every 10 bending iterations for a total of 100 bending fatigue cycles. Optical images were taken before and after 100 bending to identify major cracking of the traces. The effect of the GOx Ink storage on its viscosity was measured on Day 0 and after week long storage at 4° C. and RT using a capillary viscometer.

Enzymatic Ink-Drawn Sensors: Do-it-Yourself Renewable Glucose Sensor Strips

Figure 8:
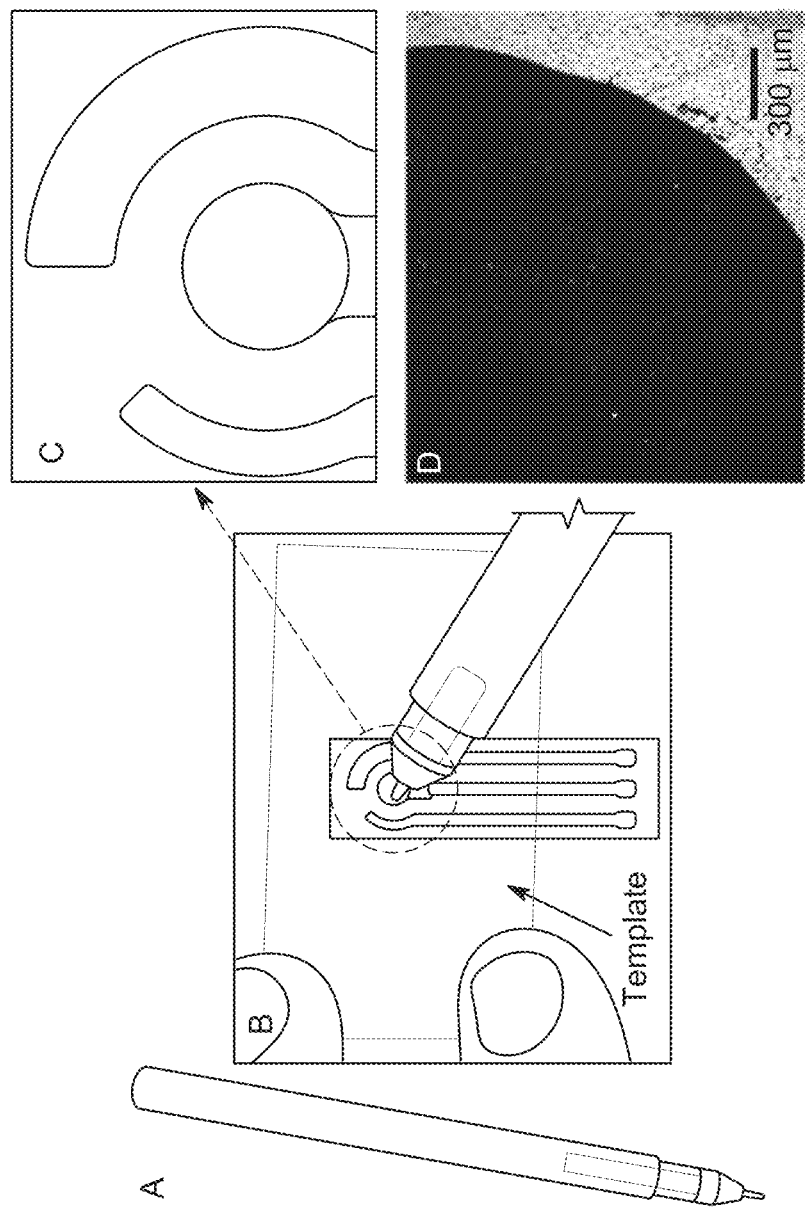
FIG. 8 shows exemplary enzymatic pen-based DIY renewable blood glucose sensors. Photograph showing (A) a GOx Ink-filled enzymatic roller pen, (B) drawing of the active enzyme layer onto a bare sensor strip using a GOx Ink-filled pen and a template, (C) a close-up view, and (D) microscopic image of a sensor surface with the active enzyme layer drawn using the enzymatic pen.

FIG. 8 shows Enzymatic pen-based DIY renewable blood glucose sensors. Photograph showing (A) a GOx Ink-filled enzymatic roller pen, (B) drawing of the active enzyme layer onto a bare sensor strip using a GOx Ink-filled pen and a template, (C) a close-up view, and (D) microscopic image of a sensor surface with the active enzyme layer drawn using the enzymatic pen. Renewable DIY glucose sensor strips were obtained by using GOx Ink-filled roller pen (FIG. 1A) and a flexible sensor strip consisting of three-electrode contingent of bare carbon counter electrode, a bare carbon electrode transducer and Ag/AgCl reference electrode. The renewable DIY glucose strips were fabricated by drawing the conducting GOx enzymatic layer using the GOx Ink-filled roller pen and a template to define the active enzyme layer area onto the bare carbon working electrode transducer followed by a 5 min air-drying (FIG. 1B). The sensor response to varying glucose concentration (0-10 mM) was measured at 0.4V in phosphate buffer (pH 7) with 1 min incubation time. A total of six electrodes were studied for analyzing electrode-to-electrode reproducibility. The renewable nature of the enzyme-drawn glucose strips was studied by wiping off the active GOx layer after each glucose test with the help of a moist cotton swab to obtain the underlying bare carbon transducer surface. Thereafter, a 'fresh' active GOx layer was redrawn on the sensor surface using the enzymatic pen and the template for the next glucose test. The reusability of the sensor strip was studied for a total of 20 reuse run cycles by exposing the same renewable sensor to a 2 mM glucose solution for each test cycle.

The ability of the renewable glucose sensor strips to detect changes in blood glucose levels was also studied in undiluted blood samples. Blood samples were obtained from a consenting human subject in fasting state and 10 min after meal consumption. The blood samples were analyzed using the renewable glucose sensor strip, and the response was correlated to that obtained using a commercial blood glucose meter (Accu-Chek Aviva Plus®). The subject was recruited in response to follow-up from flyers posted within the university. Prior to the study, the subject was prescreened and a signed consent form was obtained. The study was performed in strict compliance with the protocol that was approved by the institutional review board (IRB) at the University of California, San Diego.

Do-it-Yourself Enzymatic Sensors Drawn on Unconventional Surfaces: Epidermal Glucose Sensors The customized biocompatible ink-based roller pens were used to draw the glucose sensor directly onto the epidermis of a consenting human subject. The working electrode consisted of GOx electrode drawn using GOx Ink-filled roller pen while the counter/reference electrode was prepared using a Gr Ink. Initially, the mechanical resiliency of the DIY epidermal sensors to repeated strenuous stress cycles was studied by visually analyzing the epidermal sensor for electrode cracking before and after deforming the sensor by repeated torsional, pinching, twisting and stretching stress. The sensor was subjected to 10 fatigue cycles for each type of stress.

Finally, an epidermal glucose sensor—consisting of GOx Ink-based working electrode and Gr Ink-based counter/reference electrode—was drawn on a human subject's wrist followed by air drying for 5 min. Each electrode had an active area of 5 mm×3 mm. Thereafter, the DIY sensor was subjected to increasing glucose concentrations from 0-10 mM and the response was measured at 0.4V with 1 min incubation time. After completion of the study, the glucose sensor was removed by gentle washing of the skin with soap and water.

Environmental Phenolic Sensors

Tyr Ink-based roller pen was used to draw the working electrode while Gr Ink-filled roller pen was used to develop the counter/reference electrode directly on the plant leaves for in-situ environmental monitoring of phenols. Each electrode had a 5 mm×3 mm active area. Upon complete air drying of the DIY phenolic sensor (~30 min), it was exposed to varying levels of phenolic pollutants (p-chlorophenol or catechol). The sensor response was measured at −0.3V with an incubation time of 2 min.

Result and Discussions: Rationale for Enzymatic Ink Composition

A major aim of the work was to develop biocatalytic inks that could be used to directly incorporate inexpensive sensors on diverse surfaces for broad range of resources and applications. The composition of the new enzymatic inks has thus been optimized for combining high enzymatic stability and electrical conductivity with reproducible writing, efficient flow through the ballpoint tip, biocompatibility and strong surface adherence. Biocompatibility was a major factor considered while selecting every material of the enzymatic inks. PEG has been widely used as a binder for various ink formulation and its biocompatibility can be gauged by the fact that it is used for various drug delivery applications and as an anti-biofouling polymer for implantable devices. Thus, PEG was considered as a binder for the enzymatic inks. In order to make the inks conductive, graphite powder was used as the conductive component. Graphite has also been widely considered as benign for various biomedical use. Initially, bare carbon ink was prepared by thoroughly dissolving 30 wt % graphite in PEG solution (60 wt. % in water). It was observed that higher graphite or PEG content led to clogging of the pen. Preliminary experiments consisting of drawing traces of this ink on alumina surface followed by incubation in buffer revealed that the traces dissolved easily. This observation reflects the high solubility of PEG in water. In order to enhance the adherence of the ink to the substrate, chitosan solution (1 wt % in 0.1M acetic acid) was considered since chitosan is soluble only in acidic media while most potential applications of the enzymatic ink involve a near-neutral pH media. However, the carbon ink consisting of 30 wt % graphite in the chitosan solution displayed poor flow through the pen's nib. Hence, a mixture of PEG and chitosan was considered as a binder for the enzymatic ink. Upon studying various ratios of the two polymer binders, the best performance was obtained for a mixture containing PEG and chitosan solutions in the 2:1 (v/v) ratio. Strong hydrogen bonding between water molecules and functional groups of enzymes can cause the enzymes to undergo conformational changes when dissolved in aqueous media. Extended periods of exposure to aqueous media thus lead to decreased enzymatic activity and sensor performance. Hence, efforts were made to identify a biocompatible enzyme stabilizer for the enzymatic inks. Xylitol, a commonly used sugar substitute, has been used to stabilize enzymes in aqueous media even under thermal stress, and was thus selected here as a stabilizing agent for GOx and Tyr Inks. Additionally, xylitol and PEG may also help maintain enzyme activity at high temperatures for scenarios where ambient temperatures can reach elevated levels. Optimizing the amount of the xylitol revealed that a 2M concentration yields the best results. It was also noted that xylitol enhanced the adhesion of the ink to substrates thus extending the sensor life in aqueous media. Electron-transfer mediator methylene green was also added to the ink at 0.1 wt % to facilitate low-operating potential for glucose detection. It was noted that a 30 min sonication after each step involved in the synthesis resulted in a homogeneous ink essential for smooth drawing of reproducible biocatalytic sensors.

Stability of Inks

Ink stability is extremely critical for optimal sensor performance in view of the reduced enzymatic activity associated with conformational changes of GOx. The GOx Ink was thus extensively characterized to study its storage stability over extended periods. The effect of xylitol as an enzyme-stabilizing agent as well as the effect of storage temperature was studied using spectroscopic, thermal, viscometric and electrochemical methods as discussed in the following sections.

Amperometric Methods

Figure 9:
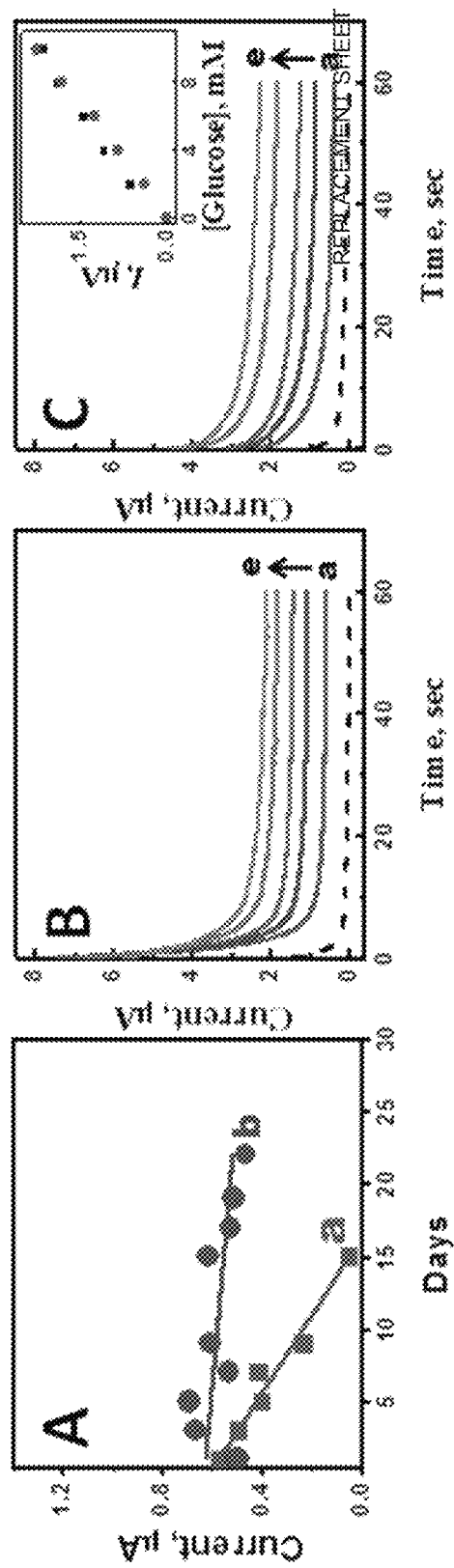
FIG. 9 shows exemplary electrochemical ink stability studies. (A) Response to 2 mM glucose over a 21 day period obtained from sensors drawn using No-Xyl GOx Ink (plot 'a') and GOx Ink (plot 'b')-filled enzymatic roller pen. Amperograms for increasing glucose concentrations from 0 (dash) to 10 mM (e) for sensors drawn on (B) Day 0 and (C) Day 21 using GOx Ink-filled enzymatic roller pen. Inset: calibration plot for sensor drawn on Day 0 (black) and Day 21 (red). Phosphate buffer (pH 7.0) and potential step to 0.4 V.

FIG. 9 shows exemplary electrochemical ink stability studies. (A) Response to 2 mM glucose over a 21 day period obtained from sensors drawn using No-Xyl GOx Ink (plot 'a') and GOx Ink (plot 'b')-filled enzymatic roller pen. Amperograms for increasing glucose concentrations from 0 (dash) to 10 mM (e) for sensors drawn on (B) Day 0 and (C) Day 21 using GOx Ink-filled enzymatic roller pen. Inset: calibration plot for sensor drawn on Day 0 (black) and Day 21 (red). Phosphate buffer (pH 7.0) and potential step to 0.4 V. The stability of the GOx enzyme in the ink was studied using amperometric measurements. The stabilizing efficacy of xylitol was monitored by evaluating sensors obtained by using freshly prepared GOx Ink and No-Xyl GOx Ink. Each type of sensor was subjected to increasing glucose concentration (0-10 mM) and the response was measured at 0.4V. The respective pens were stored at 4° C. when not in use. The ability of the sensors, developed using the two inks, to detect glucose was evaluated on every alternate day—over a three-week period—by exposing fresh sensors (n=3) to a 2 mM glucose solution. The results obtained in this study are shown in panel A. It can be clearly noticed that the response of sensors prepared with the No-Xyl GOx Ink gradually decreased with time and the sensors completely failed to respond to glucose after 2 weeks. In contrast, the sensors prepared with the xylitol-containing GOx Ink provided a nearly constant response over the entire 3-week period of the study. This observation indicates the efficacy of xylitol in stabilizing the enzyme within the ink over extended periods of storage. The ability of GOx Ink-based sensors to respond to varying glucose levels was also examined on Day 0 (Panel B) as well as at the end of the storage study, i.e., on Day 21 (Panel C). Note the nearly identical current signals. The inset in FIG. 2C exhibits the calibration curve for the sensor drawn on Day 21 superimposed on that obtained on Day 0. The data clearly demonstrates that the enzyme in the GOx Ink is stable even when stored for long durations.

Spectroscopic, Viscometric and Thermal Characterization of the Enzyme Ink

Figure 10:
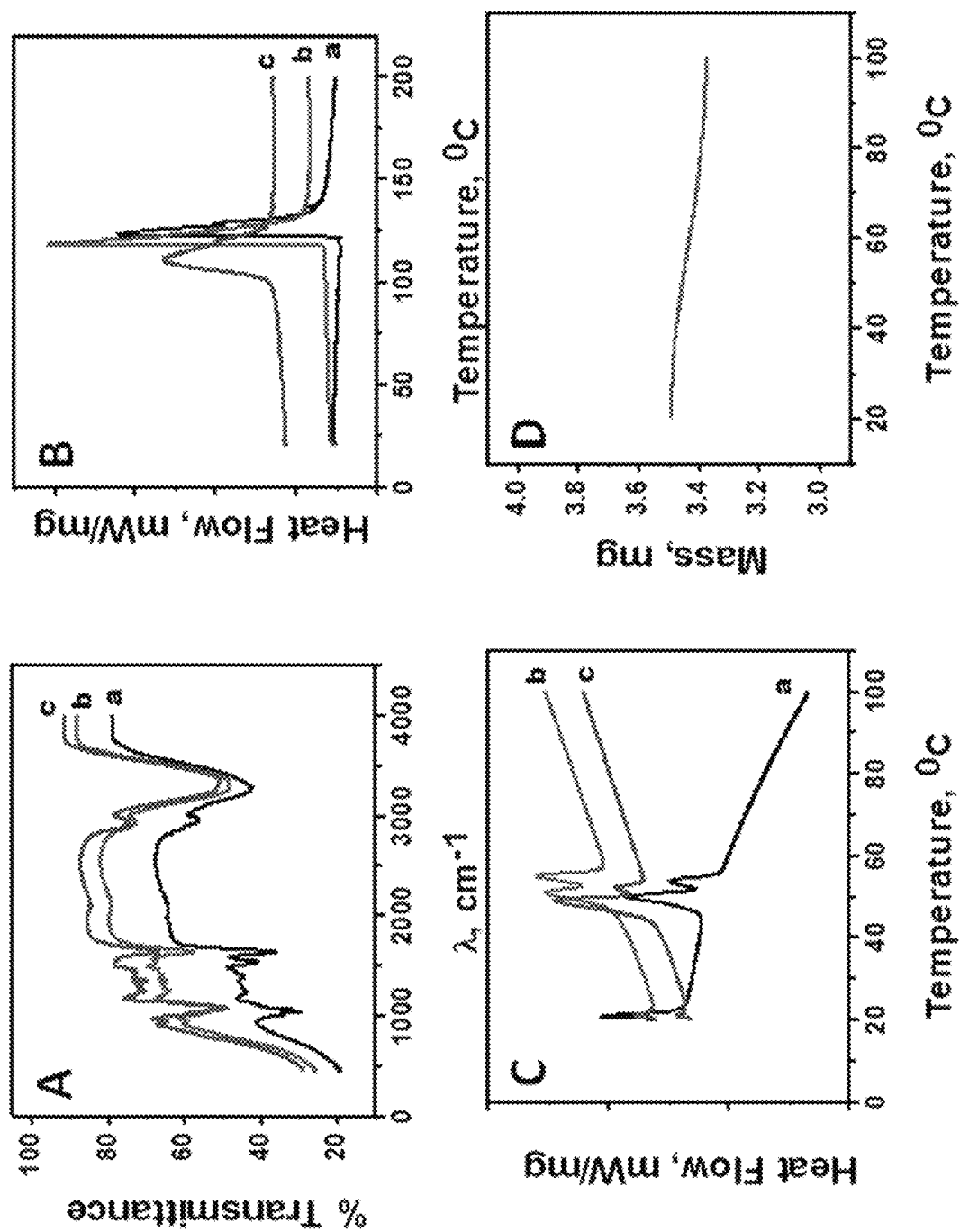
FIG. 10 shows in (A) FT-IR and (B) DSC scans for the GOx Ink. In (C) DSC and (D) TGA scans for GOx Ink cured for 5 min at 50° C. are shown. For each figure plot 'a' represents data for Day 0, plot 'b' for Day 7 when stored at RT and plot 'c' for Day 7 when stored at 4° C.

FIG. 10 shows in (A) FT-IR and (B) DSC scans for the GOx Ink. Panels (C) shows DSC and panel (D) shows TGA scans for GOx Ink cured for 5 min at 50° C. For each figure plot 'a' represents data for Day 0, plot 'b' for Day 7 when stored at RT and plot 'c' for Day 7 when stored at 4° C. The stability of the GOx Ink was also thoroughly studied using FT-IR, DSC and TGA techniques. FT-IR studies involved recording transmittance spectra over the 400-4000 cm$^{-1}$ range for a freshly prepared GOx Ink. Characteristic peaks for O—H (stretching), N—H (stretching), N—H (bending), C—O (stretching), C=O (stretching) and C—H (stretching) are clearly visible in FIG. 3 A (plot 'a'). The FT-IR spectra were recorded again after a week-long storage of the GOx Ink at 4° C. and RT to study the effect of the storage procedure on the functional groups of the various constituents of the GOx Ink. As shown in FIG. 10, panel A, the peak positions for major functional groups remain nearly identical for GOx Ink stored at RT (plot 'b') and when stored at 4° C. (plot 'c'), as compared to that for freshly prepared GOx Ink (plot 'a'). The study reveals that the functional groups remain unaffected by the storage of GOx Ink and that the mode of storage has minimal effect on the functional groups.

The next characterization study focused on evaluating the effect of storage on the secondary and tertiary structures of the polymer binders and GOx enzyme. Viscometry has been widely considered as a viable technique to study binder degradation caused by variation in the secondary and tertiary structures. Hence, the viscosity of the freshly prepared GOx Ink and ink stored for 1 week at RT and 4° C. was measured. It was noted that the viscosity for GOx ink stored at 4° C. (11.65±1.83 mNs/m$^2$) was slightly lower than freshly prepared ink (12.74±0.67 mNs/m$^2$) while the viscosity for GOx ink stored at RT decreased significantly (7.54±1.08 mNs/m$^2$). The viscometric study thus reveals that the GOx Ink stored at 4° C. is more stable in contrast to the ink stored at RT. DSC is another invaluable tool for studying thermal stability of polymers. This technique was thus utilized to further study the effect of the storage procedure for the GOx Ink. DSC scans for freshly prepared GOx Ink and inks stored at RT and 4° C. for 1 week reveal an endothermic peak around 123° C. (FIG. 10, panel B plot 'a'), 118° C. (FIG. 10, panel B plot 'b') and 110° C. (FIG. 10, panel B plot 'c'), respectively. This endothermic peak can be attributed to vaporization of water molecules bound to polymer binders and GOx. Polymer binders aid the adherence of the ink to the underlying substrate. Hence, studying the stability of the polymer after curing of the ink is crucial. This aspect was analyzed by performing DSC for GOx Ink cured at 50° C. for 5 min. FIG. 10, panel C exhibits the output for this study for freshly prepared ink (plot 'a'), and inks stored at RT (plot 'b') and 4° C. (plot 'c'). Distinct doublet endothermic peaks were observed for all the three samples. These peaks can be attributed to the melting of PEG binder. DSC scans under similar conditions were also performed for chitosan and PEG solutions. These control experiments revealed a flat scan for chitosan solution while similar doublet peaks were observed for PEG solution. This indicates that the doublet peaks in the GOx Inks are due to PEG melting. The specific enthalpies for the melting process were also calculated to obtain valuable information about the thermodynamics and thus ultimately regarding the stability of the polymer structure upon curing. The total specific enthalpy for the freshly prepared GOx Ink was found to be 27 J/g. It decreased slightly to 26.3 J/g for the GOx Ink sample stored for a week at 4° C. However, the specific enthalpy decreased significantly to 21.58 J/g for the GOx Ink stored at RT. This data indicates that the GOx Ink, when stored at 4° C., is more stable than when kept at RT and is thus supported by the results obtained from viscometric studies. The effect of curing on the mass change of the ink was also studied by TGA. FIG. 3D reveals the TGA plot for GOx Ink cured at 50° C. for 5 min. A small decrement of 0.1 mg was observed which could be due to evaporation of residual water from the cured ink. Absence of any major drastic changes in the mass of the sample indicates that the polymer binders do not degrade into small subunits within this temperature range.

Quality and Mechanical Resiliency of Ink Traces

Figure 11:
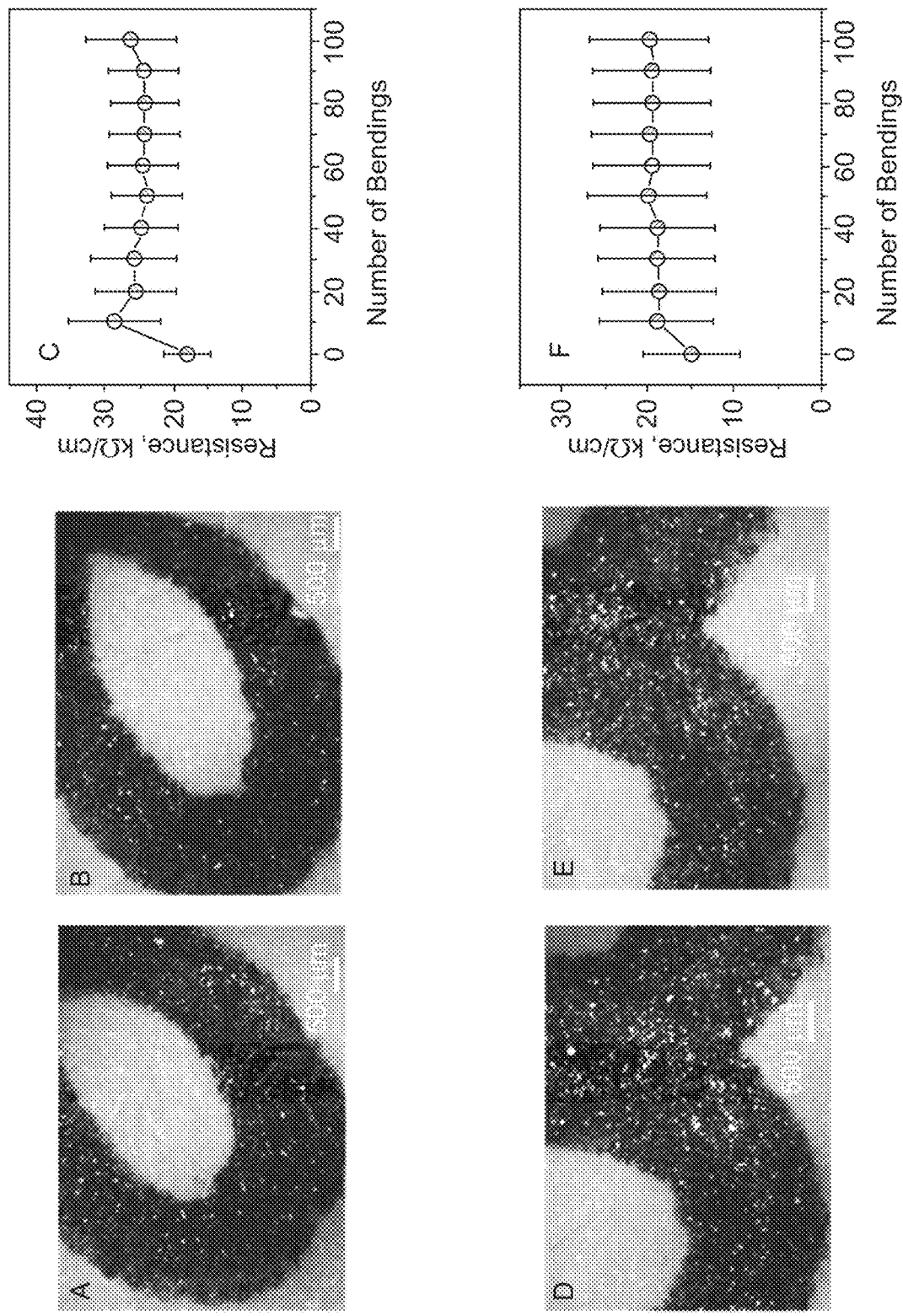
FIG. 11 shows mechanical resiliency of conductive traces drawn using biocompatible inks. Optical microscopic images (A) before and (B) after 100 bending cycles of traces drawn using Gr Ink; (C) corresponding variation in the resistance. Microscopic images (D) before, (E) after 100 bending cycles of traces drawn using GOx Ink and (F) corresponding variation in the resistance.

FIG. 11 shows exemplary mechanical resiliency of conductive traces drawn using biocompatible inks. Optical microscopic images (A) before and (B) after 100 bending cycles of traces drawn using Gr Ink; (C) corresponding variation in the resistance. Microscopic images (D) before, (E) after 100 bending cycles of traces drawn using GOx Ink and (F) corresponding variation in the resistance. The synthesized inks are expected to provide uniform and reproducible traces for realizing high-fidelity biosensors. Preliminary studies aimed at analyzing the quality of the ink transfer onto printer paper. It was noted that the biocatalytic ink was transferred smoothly onto the printer paper with minimal ink smudging (as illustrated in video 1: supplementary information). Close microscopic visualization (e.g., FIG. 11, panel A) revealed the well-defined appearance of the biocatalytic traces, with minimal cracking or edge defects and reproducible line widths. A reproducibility study resulted an average trace width of 800 μm and a low R.S.D. of 2.61% (n=5), indicating the ability of the bioactive pens to produce uniform traces. The inks have been developed to incorporate enzymatic electrochemical sensors on wide variety of rigid as well as flexible surfaces. These sensors are thus expected to withstand deformations experienced when the underlying substrate is mechanical stressed. The mechanical resiliency of Gr Ink and GOx Ink was studied by drawing conductive traces on printer paper and subjecting it to repeated 180° bending stress. Each bending cycle comprised of bending the conductive trace by 180° and holding it in this stress position for 5 sec before release. Optical images and resistance measurements were taken to assess possible cracking due to such mechanical stress. These optical observations revealed minimal damage before and after 100 bending iterations of the drawn Gr Ink traces (FIG. 11, panel A vs FIG. 11, panel B). On the other hand, resistance study concludes that the resistance of these traces increases for the first 10 bending cycles and then remains relatively stable (FIG. 11, panel C). Similar results were also observed for the traces drawn using the GOx Ink during optical (FIG. 11, panels D, E) and resistance (FIG. 11, panel F) evaluations. This set of experiments thus concludes that the biocatalytic-conducting traces adhere strongly to the underlying substrate and can thus withstand repeated bending stress with minimal effect on their conductivity. The adherence of the ink to the paper can be attributed to the strong binding between the chitosan and PEG binders and the paper surface. Overall, this behavior and images underscore the high-quality drawing ability of the enzymatic pens.

Do-it-Yourself Renewable Glucose Sensor Strips

Figure 12:
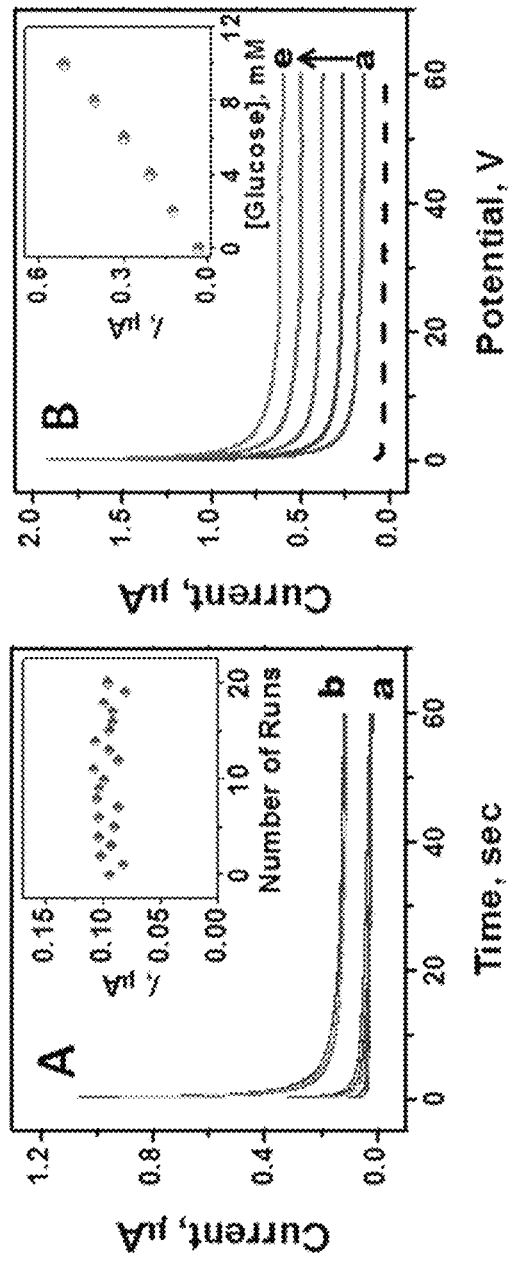
FIG. 12 shows exemplary renewable DIY glucose sensor strips. (A) Amperometric response obtained from a single renewable sensor strip for 0 mM (a) and 2 mM (b) glucose concentrations for a total of 20 repeated runs. Inset: response for each of the 20 reuse cycles. (B) Typical amperograms for increasing glucose concentrations from 0 mM (dash) to 10 mM (e) obtained from a DIY glucose sensor strip, along with the corresponding calibration plot (inset; n=6). Other conditions, as in FIG. 9.

FIG. 12 shows examples of renewable DIY glucose sensor strips. Panel (A) shows an amperometric response obtained from a single renewable sensor strip for 0 mM (a) and 2 mM (b) glucose concentrations for a total of 20 repeated runs. Inset: response for each of the 20 reuse cycles. Panel (B) shows a typical amperograms for increasing glucose concentrations from 0 mM (dash) to 10 mM (e) obtained from a DIY glucose sensor strip, along with the corresponding calibration plot (inset; n=6). Other conditions, as in FIG. 9. A major aim of the work was focused on utilizing the GOx Ink-based roller pens for developing low-cost DIY renewable glucose sensor strips towards low-resource diabetes management. This goal was achieved by simply drawing the active enzyme layer directly on a screen printed bare carbon transducer (FIG. 8, panel B). Upon completion of the test, the "used" enzyme layer was wiped off completely (along with the sample) by a moist cotton swab to regenerate the bare carbon surface for subsequent use. Repeated glucose testing on 'fresh' enzyme electrodes can be accomplished by repeating this process. Close-up view (FIG. 8, panel C) and microscopic image (FIG. 8, panel D) of the sensor surface after drawing of the active enzyme layer reveal that a uniform coating of the enzyme layer with high-quality line-edge-roughness can be achieved using the enzymatic roller pens. The active electrode area plays a crucial role in defining sensor response. A circular-shape template was thus utilized to draw reproducible sensors. The renewable nature of the sensor strips was studied by repeatedly using the same sensor strip with freshly drawn enzyme layers for measuring glucose concentration (2 mM) for a total of 20 times. After each test, the "used" enzyme layer was wiped off and a "new" DIY enzyme layer was drawn on the sensor strip for the subsequent test. FIG. 12, panel A displays amperograms for 20 consecutive tests performed on the same sensor strip, while the inset shows the variation in the sensor response over this series of 20 tests. The reproducibility of the DIY renewable glucose sensors is clearly evident from this study (R.S.D.~8%). This underscores the precision of uniformly transferring fixed amount of biocatalytic ink while drawing the active and reproducible enzyme layer by these pens, as well as the homogeneous ink composition. The response for sensor strips for varying glucose concentrations was also studied. FIG. 12, panel B reveals typical amperograms for increasing glucose concentrations, while the inset displays the mean calibration curve obtained for six different electrodes.

Figure 13:
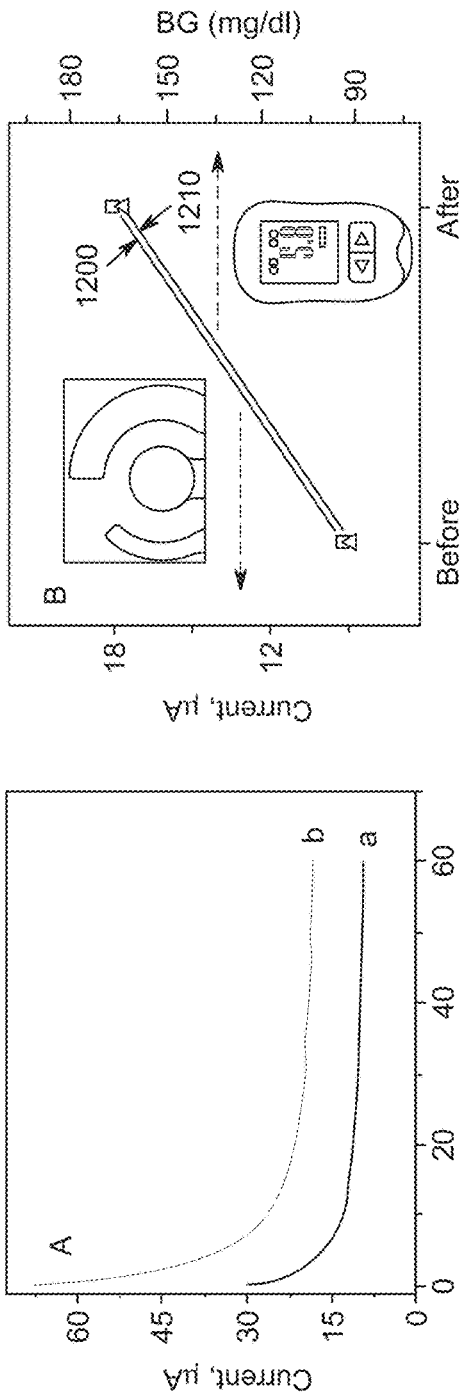
FIG. 13 shows exemplary renewable DIY glucose sensor strips for glucose monitoring in undiluted blood samples. (A) Amperogram obtained in fasting state (a) and after consumption of a meal (b). (B) Response of the renewable DIY sensor (black) in correlation with that obtained from a commercial glucose meter (red).

FIG. 13 shows exemplary renewable DIY glucose sensor strips for glucose monitoring in undiluted blood samples. Panel (A) shows an amperogram obtained in fasting state (a) and after consumption of a meal (b). Panel (B) shows a response of the renewable DIY sensor (1200) in correlation with that obtained from a commercial glucose meter (1210). The renewable DIY glucose sensor strips were then utilized for detecting glucose levels in undiluted blood samples. Blood samples were taken from the fingertip of a consenting human subject in fasting state and 10 min after consumption of meal. FIG. 13, panel A displays the amperograms obtained from the sensor strip before (plot 'a') and after (plot 'b') meal consumption. The renewable sensor response was also correlated with that obtained from commercial single-use sensor strip-based blood glucose meter (FIG. 13, panel B), indicating the ability of renewable DIY sensor strips to detect glucose in undiluted blood samples.

Do-it-Yourself Epidermal Glucose Sensors

Figure 14:
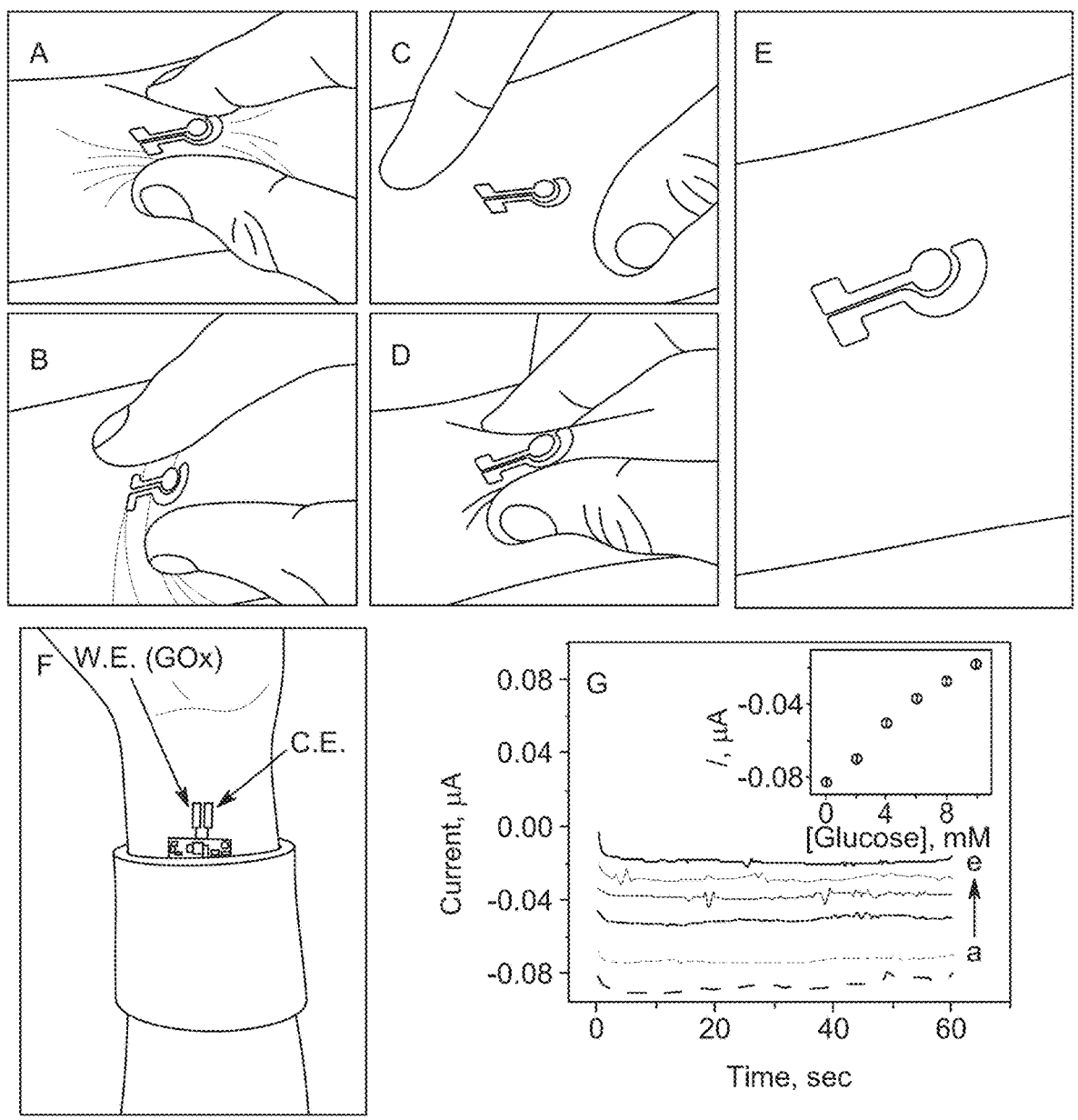
FIG. 14 shows exemplary DIY epidermal glucose sensors. Photographs of sensor when subjected to repeated (A) twisting, (B) torsional, (C) stretching and (D) pinching and (E) after a total of 100 stress cycles. (F) Epidermal glucose sensor coupled with a Bluetooth-enabled potentiostat (envision) for continuous epidermal glucose monitoring. (G) Sensor response, obtained directly on the skin, for increasing glucose levels from 0 (dash) to 10 mM (e). Inset: calibration plot for the epidermal glucose sensor. Other conditions, as in FIG. 2.

FIG. 14 shows exemplary DIY epidermal glucose sensors. Photographs of sensor when subjected to repeated (A) twisting, (B) torsional, (C) stretching and (D) pinching and (E) after a total of 100 stress cycles. Panel (F) shows an exemplary epidermal glucose sensor coupled with a Bluetooth-enabled potentiostat (envision) for continuous epidermal glucose monitoring. Panel (G) shows an exemplar sensor response, obtained directly on the skin, for increasing glucose levels from 0 (dash) to 10 mM (e). Inset: calibration plot for the epidermal glucose sensor. Other conditions, as in FIG. 9. Taking advantage of the freedom offered by the enzymatic ink-based roller pens to incorporate sensors directly on unconventional complex surfaces, the GOx Ink-based roller pen was utilized to draw glucose sensor directly on the skin of a consenting human subject. This study indicated high quality and uniform biocatalytic traces on irregular, soft and complex surfaces, such as the human skin. It was noted that an average trace width of 1 mm could be drawn by the enzyme pens (R.S.D.: 3.2%; n=5). Epidermal devices continuously experience mechanical deformations due to routine bodily movements and hence must withstand such stress without major loss in their performance. The resiliency of DIY epidermal glucose sensor was thus evaluated by repeatedly deforming it via twisting (FIG. 14, panel A), torsional (FIG. 14, panel B), stretching (FIG. 14, panel C) and pinching (FIG. 14, panel D) stressors. Visualizing the sensor after a total of 100 such stress cycles revealed minimal damage to it (FIG. 14, panel E), reflecting the ability of the epidermal sensor to endeavor mechanical deformations.

Thereafter, a two-electrode DIY glucose sensor was drawn on the wrist of a consenting subject for epidermal detection of glucose. Such a sensor can be easily interfaced with a Bluetooth-enabled wearable potentiostat, as envisioned in FIG. 14, panel F. The epidermal detection of glucose using the pen-drawn sensor revealed a linear sensor response in the 0-10 mM range (FIG. 14, panel G). This corroborates the capacity of the DIY sensor to detect glucose directly on the human skin. It should be noted, however, that the glucose epidermal sensor was studied as a proof-of-concept for the enzymatic ink-based epidermal sensors, and biocatalytic inks for other relevant analytes, e.g. lactate, can be prepared in a similar fashion for epidermal non-invasive health monitoring.

Do-it-Yourself Environmental Phenolic Sensors

Figure 15:
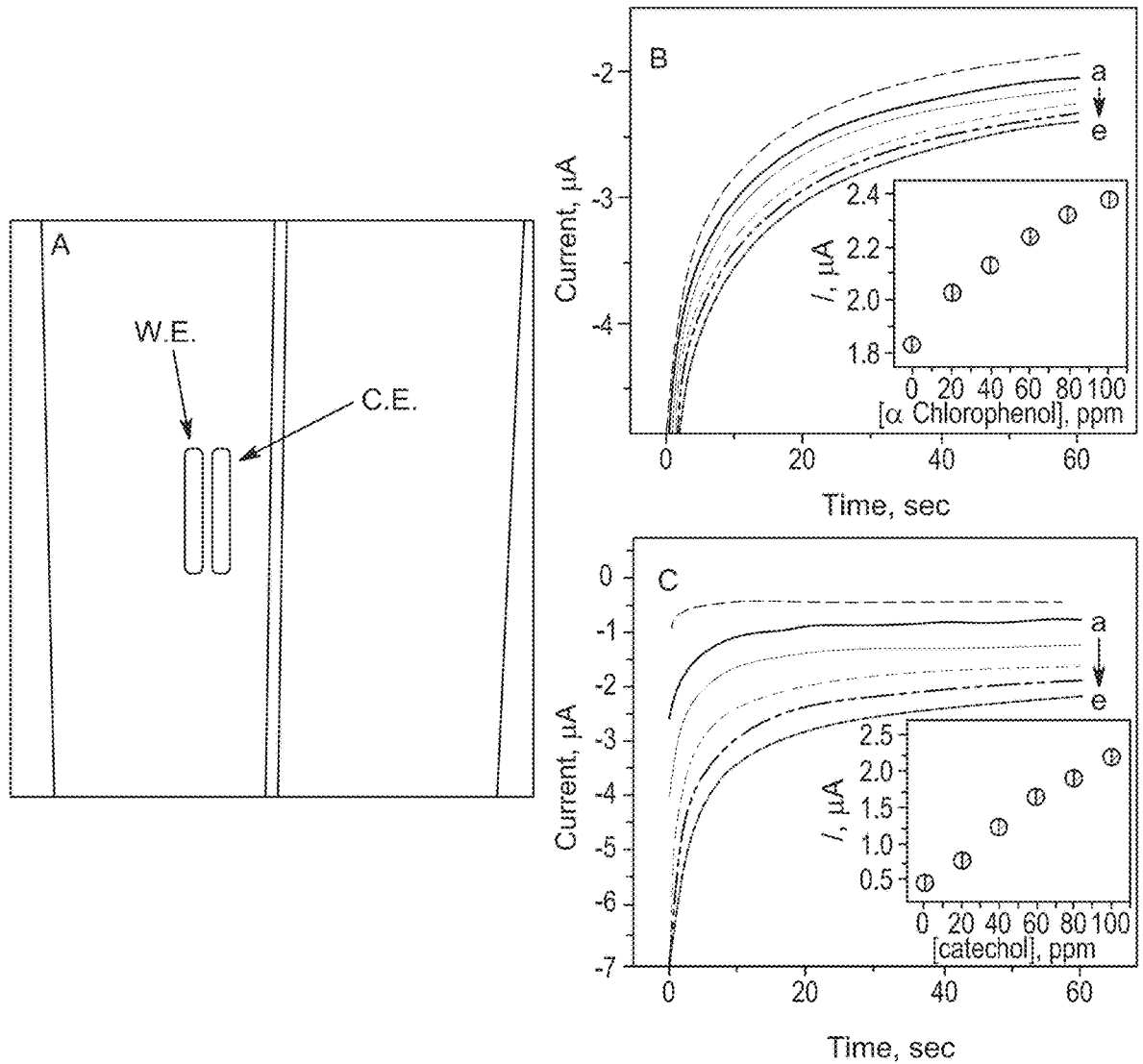
FIG. 15 shows and exemplary leaf-based DIY phenolic sensors. (A) Snapshot of a phenolic sensor drawn directly on a leaf using Tyr Ink-based roller pen. Response to increasing (B) p-chlorophenol and (C) catechol concentrations (20-100 ppm, a-e) along with the background signal (dashed line), obtained directly on the leaf. Insets: corresponding calibration plots. Phosphate buffer (pH 7.0) and potential step to −0.3 V.

FIG. 15 shows an exemplary leaf-based DIY phenolic sensors. (A) Snapshot of a phenolic sensor drawn directly on a leaf using Tyr Ink-based roller pen. Response to increasing (B) p-chlorophenol and (C) catechol concentrations (20-100 ppm, a-e) along with the background signal (dashed line), obtained directly on the leaf. Insets: corresponding calibration plots. Phosphate buffer (pH 7.0) and potential step to −0.3 V. The concept of writing biocatalytic layers has profound implications beyond healthcare too. For example, the enzymatic ink-based roller pens were used to directly draw environmental biosensors on plant leaves towards in-situ monitoring of target pollutants (FIG. 15, panel A). For example, the Tyr Ink-based leaf sensors were used to detect common phenolic compounds like p-chlorophenol and catechol. Amperograms for the phenols were recorded by directly exposing the leaf-based DIY phenolic sensors to increasing phenol concentrations. It is clearly evident that the sensors respond linearly to increasing p-chlorophenol (FIG. 15, panel B) and catechol (FIG. 15, panel C) levels, and thus holds considerable potential as environmental sensors. It should be noted that the concept is not limited to phenolic compounds, and the inks can be easily modified with other enzymes and reagents to detect other target pollutants, such as heavy metals or pesticides.

The disclosed technology provides various examples of enzymatic ink-based roller pens to directly draw electrochemical biosensors on various unconventional surfaces. In particular, the ability to use the enzymatic pen to draw active GOx layer for repeated blood glucose testing has been demonstrated towards diabetes testing in low-resource settings. The attractive feature of this one-step fabrication technique, as compared portable sensors, is the immense freedom available to incorporate high-fidelity inexpensive sensors of any design on a wide variety of surfaces with minimal user training. The enzymatic inks can be synthesized and extensively characterized using spectroscopic, viscometric, electrochemical, thermal and microscopic techniques. The use of such enzymatic roller pens towards the incorporation of biocatalytic sensors directly on unconventional surfaces, such as human epidermis and leaves, has also been demonstrated. The bioactive pens can fabricate inexpensive biosensors since a single 8-cm long enzymatic pen can produce approximately 500 renewable glucose sensors strips. The use of these enzymatic roller pens to write biocatalytic materials and electrochemical biosensors is not limited to the above mentioned surfaces and can be used to assimilate inconspicuous sensors on a wide range of surfaces, for example, renewable sensors drawn directly on cell-phone for personalized and low-resource diagnosis. Similarly, the enzymatic pens can be used to draw sensors directly on external building walls for monitoring toxic gas pollutants. The pens could also find variety of security applications for rapid field incorporation of inconspicuous sensors that can monitor potential threats (e.g., explosives, nerve agents). The new biocatalytic pen technology thus holds considerable promise for a broad range of sensing applications. Though the preliminary results and outlook for the enzymatic-ink based DIY sensors are quite promising, future studies should aim at analyzing sensor performance under tough conditions, for example, extreme temperatures, varying humidity, exposure to sun light and ink stability over extended periods of storage.

Examples Embodiments Using Portable User Devices

In some embodiments, repeated blood glucose monitoring may be made possible using a single bare sensor (e.g., without a permanent enzyme coating) integrated directly with a smartphone case. A stylus loaded with enzymatic pellets may be used along with and a permanent electrochemical sensor fabricated on a customized smartphone case. The stylus may be conveniently placed within a dedicated slot in the smartphone case, while the sensor (which may include a three electrode system) is integrated on the surface of the smartphone case. The electronics required for measuring, analyzing, storing and transmitting information obtained from the sensor may be integrated either within the main hardware of the smartphone or can be integrated with the smartphone case. The enzymatic pellets are synthesized to enable storing the enzyme at room temperature for extended durations without leading to deterioration of the enzymatic activity. This allows for these pellets to be stored in the pellet dispensing stylus and used for performing blood glucose measurement directly on a smartphone.

In one example test procedure, the user removes the stylus from the in-built housing and dispenses an enzymatic pellet on top of the bare (without enzyme coating) sensor surface. Thereafter, the user places the blood sample on top of the pellet-covered sensor to obtain the blood glucose level. Upon completion of the test, the used pellet can be disposed by simply wiping off the sensor surface with a moist cotton swab/napkin. Doing so leads to restoration of the bare sensor surface that can be reused for the next blood test without contamination from previous tests.

Presently, in almost all the portable glucose sensors, single use sensor strips are used in conjugation with a hand-held glucose meter. For many patients, glucose must be monitored on a regular basis and thus a patient uses several strips and the patient must carry the glucose meter with him/her throughout the day. This may cause financial burden (since the patient must use a new sensor strip for each test) and inconvenience (since the patient must always carry the device with him/her). Smartphones have become quite ubiquitous and people all over the world carry these devices throughout the day.

Considering this evolving trend of ubiquitous presence of smartphones, the disclosed techniques can be advantageously used to integrate a renewable glucose sensor within a smartphone. The user will no longer require the need to separately carry the sensor strips and the glucose meter since the renewable sensor, enzymatic pellet-based stylus and the electronics (required for acquiring, analyzing, storing and transmitting data) are integrated within the customized smartphone case.

Advantageously, the disclosed technique facilitates with complete regeneration of the active enzyme layer after every use, thus overcoming shortcomings of the presently known reusable glucose sensors that use a same reagent layer multiple times, and thus are susceptible to contamination and also subject to measurement errors due to leaching of the enzyme layer due to multiple uses. The complete regeneration of the active enzyme layer is achieved by removing the "used" enzymatic pellet by using a moist cotton swab. Thereafter, a "fresh" enzymatic pellet can be dispensed from the pellet based stylus onto the bare sensor surface for performing the next test. This technology is not limited to glucose detection and can be extended for other chemicals by modifying the composition of the enzymatic pellets.

Example Systems

Figure 16:
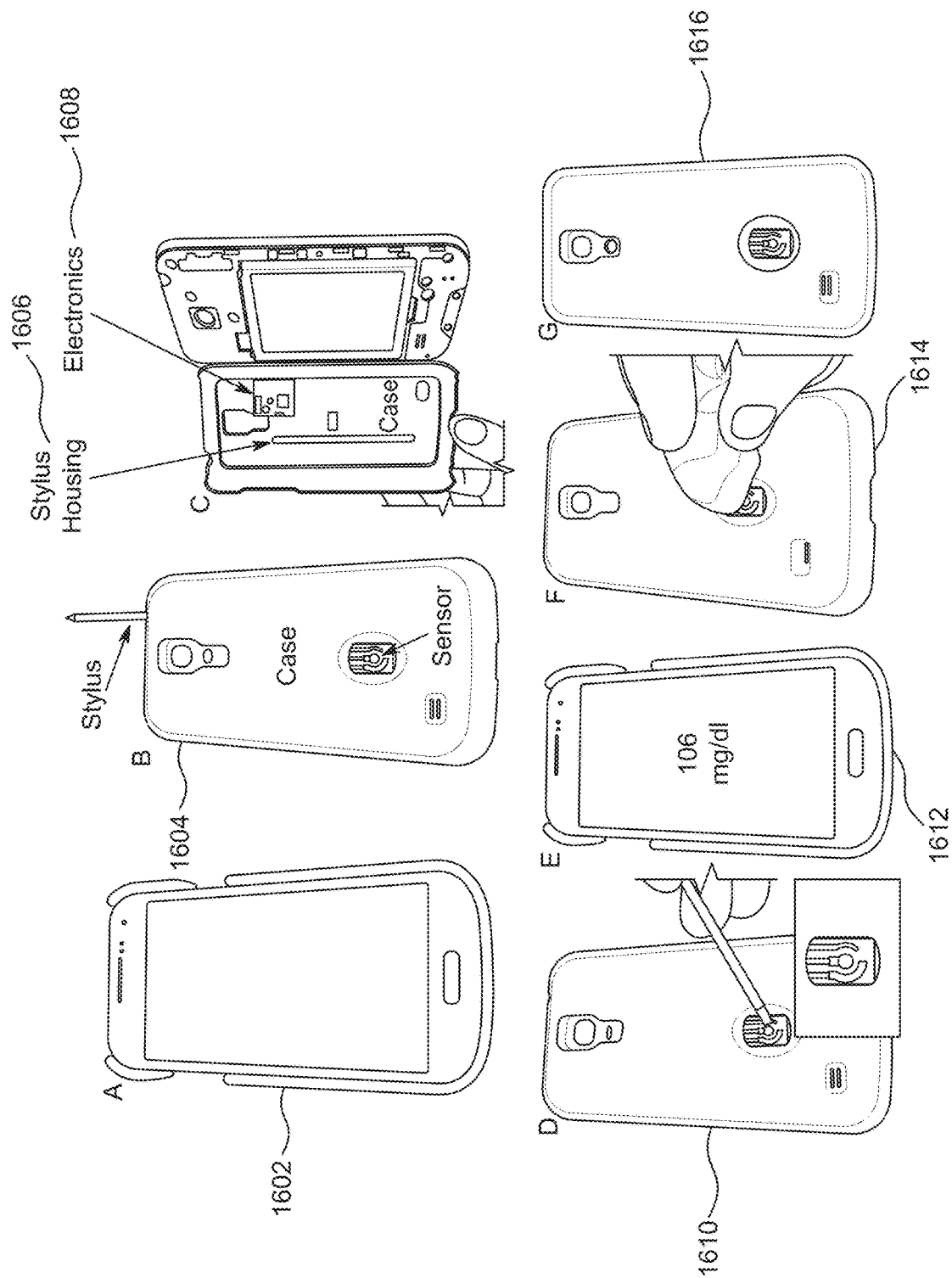
FIG. 16 shows an example of a phone case adapted to include a stylus housing that can hold a stylus and an electrochemical sensor for repeated-use testing by a user.

Some embodiments may include a customized enzymatic pellet based stylus and a screen printed "sensor strip" including a three electrode contingent and an electrochemical analyzer. The stylus, sensor as well as the electronics is integrated within a smartphone case. One example embodiment is depicted in FIG. 16.

Enzymatic pellets: The enzymatic pellet may be prepared by mixing various components, for example, but not limited to, graphite as a conductive component, silicon oil or mineral oil as a binder, rhodium on carbon as a catalyst, nickel as a magnetic component, glucose oxidase (GOx) as an enzyme and trehalose as an enzyme stabilizer. The enzyme may be lyophilized with the stabilizer or the two may be physically mixed. It should however be mentioned that the composition is not limited to the above components and other additives, for example, enzymatic mediators, additional stabilizers etc. can also be added.

The components are thoroughly mixed followed by preparing the enzymatic pellets of fixed dimensions using a pellet press machine. The enzymatic pellets are then loaded in the custom built pellet dispensing stylus which releases one pellet at a time. The pellet dispensing stylus works similar to commercial pellet pen used for dispensing pellets used in air guns.

Sensor: The electrochemical sensor may include a three electrode contingent (working, counter and reference electrode) and may either fabricated using standard printing or lithographic processes. The reference electrode could include silver/silver chloride electrode while the working and counter electrodes can be made of carbon, platinum, gold etc. The sensor can be either made separately and then integrated onto the cellphone case or it can be fabricated directly onto the cellphone case.

Cellphone case: The cellphone case will have a dedicated housing for the enzymatic pellet dispensing stylus, location to integrate the sensor and also the electronics. The case may house a small permanent electromagnet just below the working electrode of the sensor for magnetically attaching the dispensed enzymatic pellet. Such an electromagnet will enable secured attachment of the pellet to the sensor surface.

A typical test procedure may be performed as follows. While using the device (1602), the user will first remove the pellet based stylus from the casing (1604). The stylus housing 1606 and the electronics for measurement 1608 may be positioned on the case as depicted. The stylus removal may be followed by dispensing a single pellet on the sensor present on the phone case (1610). The electromagnet placed just below the sensor will be activated to hold the magnetic pellet at its location. Thereafter the user will provide a droplet of blood. Subsequently, the electrochemical analyzer 1608, integrated within the smartphone case, will be activated to quantify the glucose level present in the blood sample. The glucose concentration will then be displayed on the phone screen (1612). Alternatively, the data can be also transmitted wirelessly from the phone to other electronic devices or further analysis or storage. Upon completion of the test, the user will wipe off the blood sample and discard the "used" pellet (1614). The user will follow the same procedure for the next test (1616).

The disclosed technology has particular commercial promise in the field of diabetes management, currently dominated by the billion US dollar disposable strip industry. By integrating a renewable glucose sensor directly onto a smartphone, the user will no longer be required to carry additional sensor strips and glucose meter with him/her.

Figure 17:
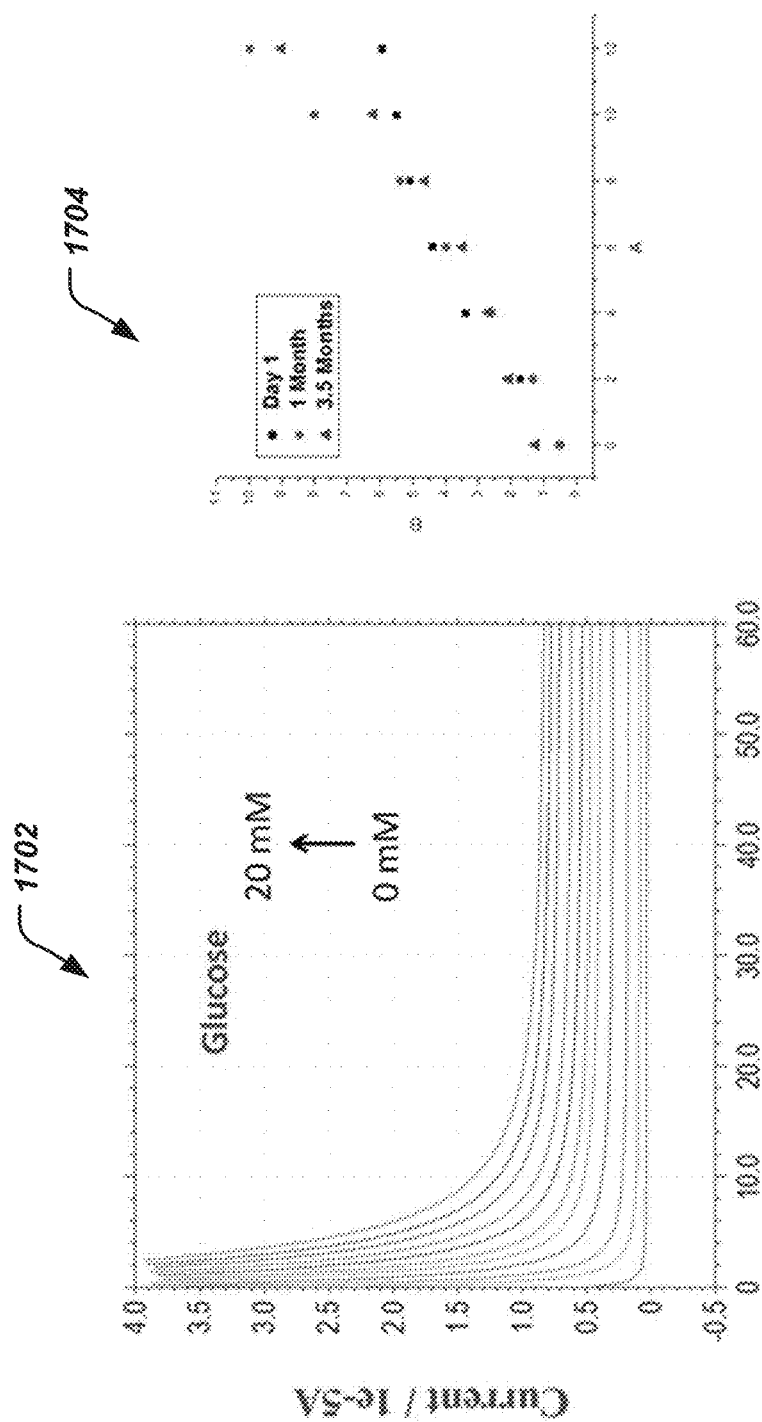
FIG. 17 shows a graph of results obtained in one example stability study for pellets prepared by mixing: 30 mg GOx lyophilizerd with 30 mg Trehalose in Phosphate Buffer (pH 7.0), 27 mg Rh—C, 122 mg Ni, 121 mg Graphite, 135 mg Silicon Oil.

FIG. 17 shows a graph of results obtained in one example stability study for pellets prepared by mixing: 30 mg GOx lyophilizerd with 30 mg Trehalose in Phosphate Buffer (pH 7.0), 27 mg Rh—C, 122 mg Ni, 121 mg Graphite, 135 mg Silicon Oil. The graph 1702 shows amperograms for increasing glucose concentration from 0 to 20 mM. The graph 1704 shows the corresponding glucose sensitivity of the instrument over a time period of use.

Figure 18:
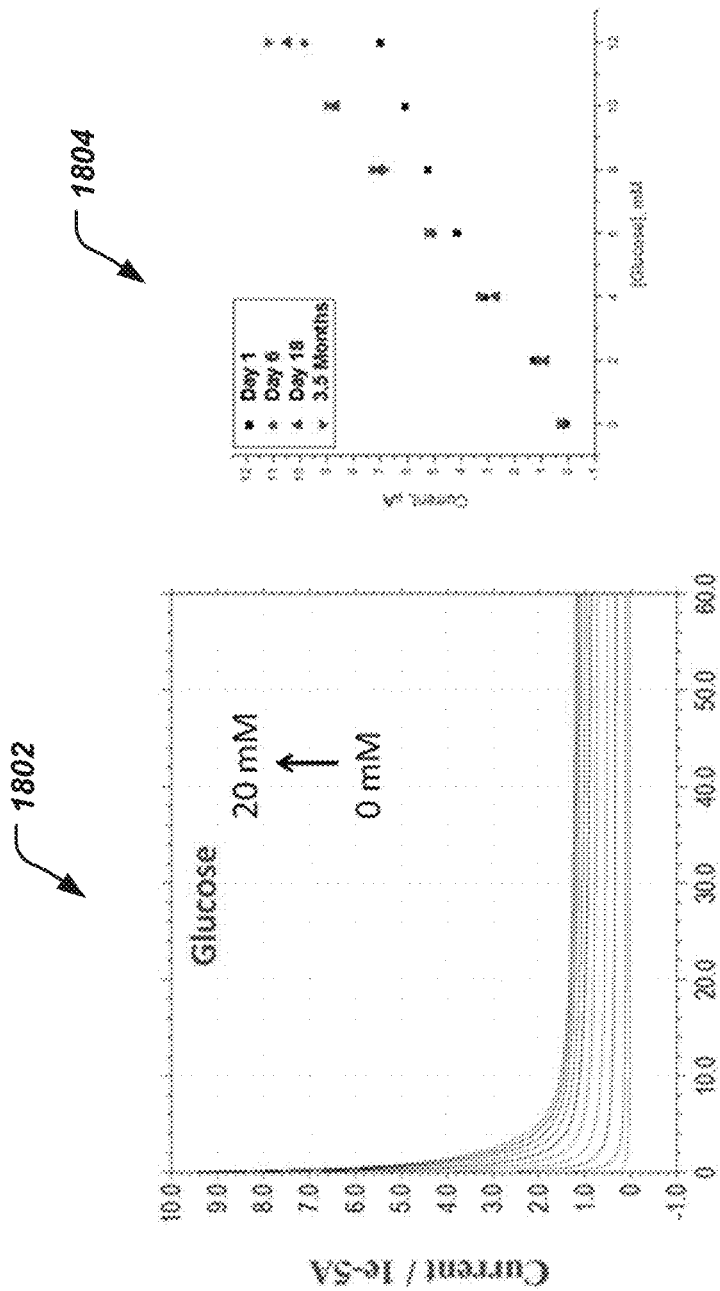
FIG. 18 shows a graph of results obtained in one example stability study for pellets prepared by mixing: 30 mg GOx, 30 mg Trehalose, 27 mg Rh—C, 122 mg Ni, 121 mg Graphite, 135 mg Silicon Oil.

FIG. 18 shows a graph of results obtained in one example stability study for pellets prepared by mixing: 30 mg GOx, 30 mg Trehalose, 27 mg Rh—C, 122 mg Ni, 121 mg Graphite, 135 mg Silicon Oil. The graph 1802 shows amperograms for increasing glucose concentration from 0 to 20 mM. The graph 1804 shows the corresponding glucose sensitivity of the instrument over a time period of use.

Figure 19:
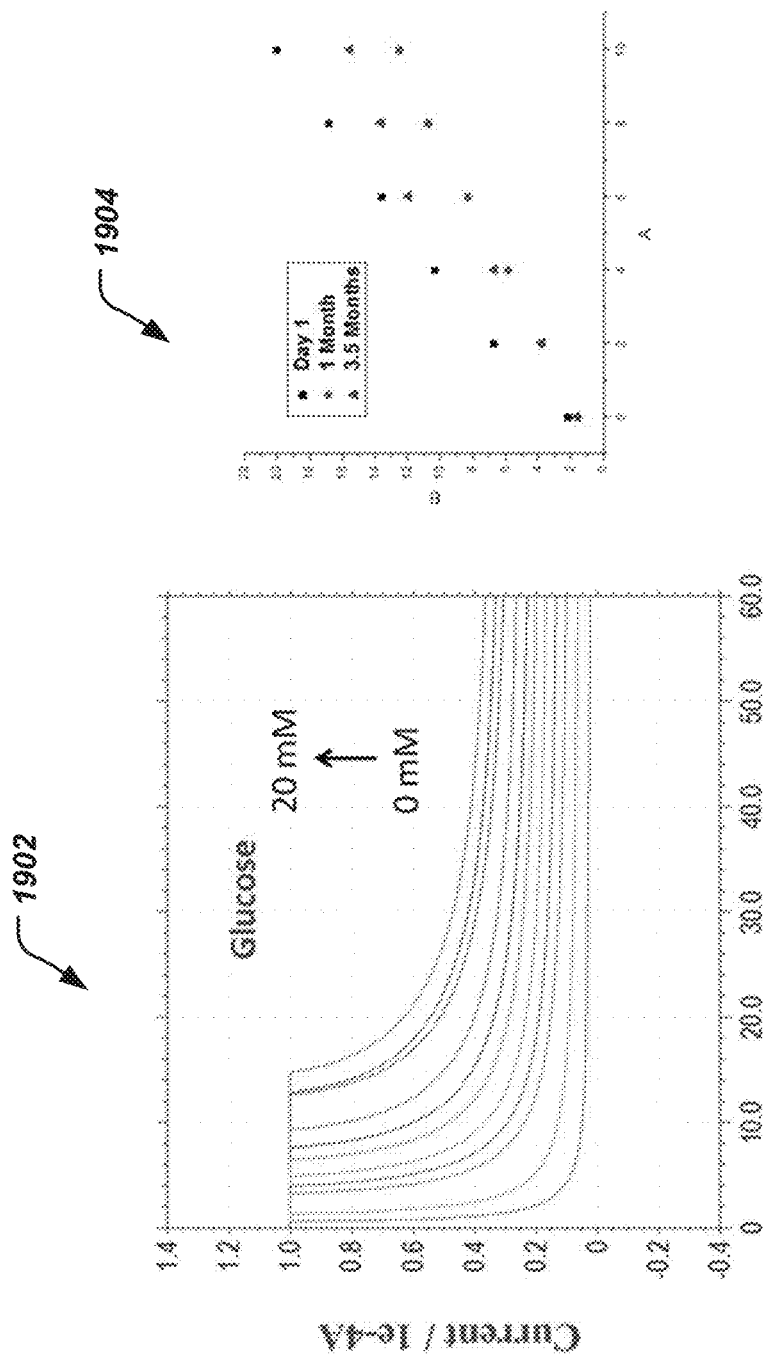
FIG. 19 shows a graph of results obtained in one example stability study for pellets prepared by mixing: 116 mg GOx lyophilizerd with 117 mg Trehalose in polyethylene glycol (60 wt % in water), 27 mg Rh—C, 122 mg Ni, 121 mg Graphite, 135 mg Silicon Oil.

FIG. 19 shows a graph of results obtained in one example stability study for pellets prepared by mixing: 116 mg GOx lyophilizerd with 117 mg Trehalose in polyethylene glycol (60 wt % in water), 27 mg Rh—C, 122 mg Ni, 121 mg Graphite, 135 mg Silicon Oil. The graph 1902 shows amperograms for increasing glucose concentration from 0 to 20 mM. The graph 1904 shows the corresponding glucose sensitivity of the instrument over a time period of use.

Figure 20:
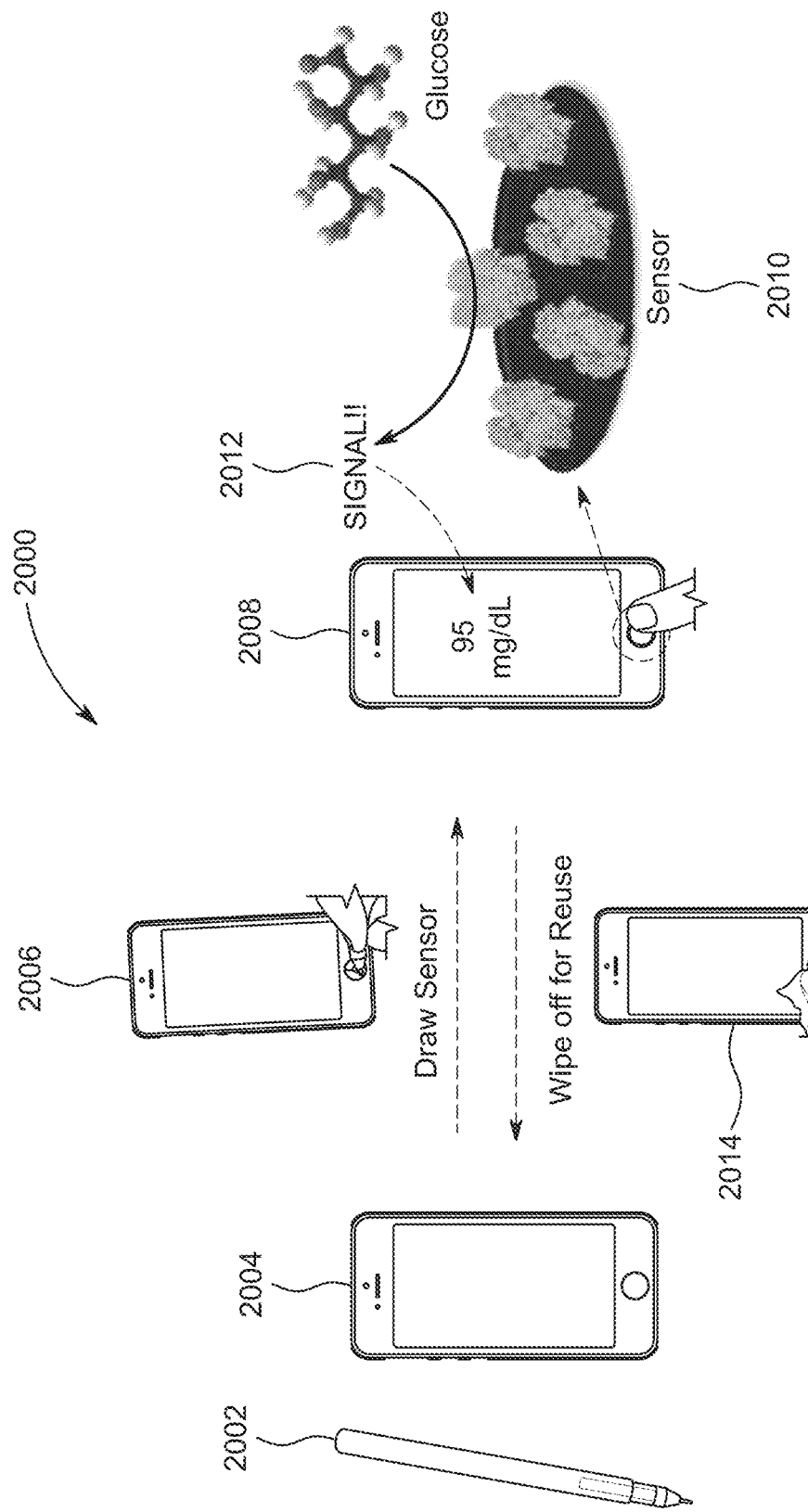
FIG. 20 depicts an example workflow for repetitive blood glucose testing by a user.

FIG. 20 depicts an example workflow 2000 for repeated blood glucose testing by a user using an embodiment of the disclosed technology. A pellet-filled stylus 2002 may accompany a user's smartphone 2004. Using the enzyme pellet loaded in the stylus, the user may draw the enzyme on a sensor area of the smartphone (2006). After depositing the enzyme on the sensor, the user may deposit blood (or other fluid to be measured) on the sensor (2008). The interaction between the sensor 2010 and the chemical being measured (e.g., glucose) may produce a signal 2012 that may be captured using the smartphone 2004. The result may be converted into a user-readable display on the user interface of the smartphone 2004, e.g., a display that reads out the concentration of the glucose (95 mg/dL). At this time, the user may wipe off the sensor (2014) such that the smartphone 2004 is now ready for additional measurements in the future.

Some embodiments may include a mobile device comprising an integrated contact pad including a sensor pattern, wherein the sensor pattern is configured to receive an enzymatic ink that includes biomaterials, and a display unit for displaying data associated with analysis performed through the enzymatic ink on the sensor pattern. The sensor pattern is configured to receive the enzymatic ink that includes an enzyme in the biomaterials. Alternatively, the sensor pattern is configured to receive the enzymatic ink that includes in the biomaterials one or more biocompatible binders, one or more biocompatible mediators, an enzyme, an enzyme stabilizer, or a conductive material. The sensor pattern may be reusable via cleaning of the sensor pattern between use by wiping. The sensor pattern may include at least two or three electrodes.

Some embodiments may be in the form of a portable apparatus, e.g., as described with respect to FIG. 16. The portable apparatus includes a dispenser having volume to hold and dispense one or more individually dispensable pellets made up of an enzyme compound, a case comprising a mechanism using which the dispenser can be attached to the case, and an electrochemical sensor attached to the case and having a reference electrode, a working electrode and a counter electrode arranged to provide a flat surface for application of the enzyme compound and a chemical for sensing and to produce an electrical signal resulting from the sensing. In various embodiments, the case may be a smartphone carrying case, a tablet carrying case or a case for carrying another portable user device, and may thus appropriately be shaped to snuggly fit the user device.

In some embodiments, e.g., depicted in 1604, the dispenser may include a stylus or pen shaped container that has an elongated body with a cavity along the length of the container. The cavity may be connected to at least one end of the dispenser and may be resealable such that a user may be able to fill multiple enzyme pellets into the cavity. The pellets may be fillable from the dispensing end, or a back end that is on the opposite side from the dispensing end. Various embodiments of the electrochemical sensors and ways for fabricating the same are described throughout the present document.

In some embodiments, the portable apparatus may also include an interface electronics, e.g., a printed circuit board with circuitry. The electronics may have a first interface on which it receives electrical signals from the electrochemical sensors and a second interface via which it communicates with a smartphone that is used as a display device to display measurement results to a user interface. The interface electronics may communicate with the smartphone via a wireless interface such as a Bluetooth or Wi-Fi interface. The smartphone may appropriately be loaded with a communication and display software app that can receive signals from the interface electronics and display human-readable results on the display screen.

Water-based enzyme inks often tend to denature the enzyme and lead to its inactivation. Some embodiments thus advantageously use silicon oil-based pellets in the presence of trehalose (enzyme stabilizer). It will be appreciated that due to complete absence of water, plus the stabilizing effect of trehalose, the enzyme generated using presently disclosed technique could easily maintain its activity up to 6-7 months even at room temperature within the pellets.

It will be appreciated that the disclosed technology has particular commercial promise in the field of diabetes management, currently dominated by the billion US dollar disposable strip industry. By using the disclosed re-usable sensor strips the financial burden on the diabetic patient population can be reduced. Furthermore, the described techniques, systems and devices can be used to incorporate sensors and biofuel cells directly on various substrates like cellphone, human skin, leaves etc. for on-site personalized diagnostics as well as environmental analysis. Thus the invention holds promise in diverse fields where electrochemical devices need to be integrated within the surrounding.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A portable enzymatic-ink dispensing and electrochemical sensing system, comprising:
   a substrate comprising a planar surface;
   an electrochemical sensor disposed on the substrate and comprising a predefined sensor pattern of electrodes, the predefined sensor pattern of electrodes including a first electrode and a second electrode disposed in a same plane on the planar surface of the substrate;
   an active enzyme layer disposed on the first electrode, wherein the active enzyme layer includes an enzymatic-ink that is drawable on and removable from the first electrode, the enzymatic ink including:
      one or more biocompatible binders,
      one or more biocompatible mediators,
      an enzyme,
      an enzyme stabilizer, and
      a conductive material; and
   a hand-held dispenser operable to draw the enzymatic ink on the first electrode to create the active enzyme layer for the electrochemical sensor, the hand-held dispenser including:
      a squeeze tube configured to hold the enzymatic-ink and be compressed in order to dispense the enzymatic-ink from the squeeze tube, and
      an applicator coupled to the squeeze tube and configured to apply the enzymatic-ink dispensed from the squeeze tube onto the substrate to form the active enzyme layer of the electrochemical sensor,
   wherein the enzymatic-ink is removable from the first electrode of the predefined sensor pattern on the planar surface of the substrate to enable production of a new electrochemical sensor having a new active enzyme layer by formation of a fresh amount of the enzymatic-ink on the first electrode.

2. The portable enzymatic-ink dispensing system of claim 1, wherein the at least one biocompatible binder includes at least one of polyethylene glycol or chitosan.

3. The portable enzymatic-ink dispensing system of claim 1, wherein the at least one biocompatible mediator includes at least one of methylene green or prussian blue.

4. The portable enzymatic-ink dispensing system of claim 1, wherein the enzyme includes glucose oxidase enzyme for detecting glucose levels.

5. The portable enzymatic-ink dispensing system of claim 1, wherein the enzyme stabilizer includes a polyhydric alcohol.

6. The portable enzymatic-ink dispensing system of claim 5, wherein the polyhydric alcohol includes at least one of xylitol, ethylene glycol, glycerol, erythritol or sorbitol.

7. The portable enzymatic-ink dispensing system of claim 1, wherein the enzyme stabilizer includes trehalose.

8. The portable enzymatic-ink dispensing system of claim 1, wherein the enzyme includes tyrosinase enzyme for detection of phenolic compounds.

9. The portable enzymatic-ink dispensing system of claim 8, wherein the phenolic compounds include at least one of p-chlorophenol or catechol.

10. The portable enzymatic-ink dispensing system of claim 1, wherein the conductive material includes graphite.

11. A method of repeatably fabricating electrochemical sensors on a substrate comprising a planar surface by applying enzymatic ink on a predefined sensor pattern of electrodes of the electrochemical sensors using a hand-held dispenser including (i) a squeeze tube configured to hold the enzymatic ink and be compressed in order to dispense the enzymatic ink from the squeeze tube, and (ii) an applicator coupled to the squeeze tube and configured to apply the enzymatic ink dispensed from the squeeze tube onto an electrode of the predefined sensor pattern of electrodes to create an active enzyme layer of an electrochemical sensor, wherein the enzymatic ink includes one or more biocompatible binders, one or more biocompatible mediators, an enzyme, an enzyme stabilizer, and a conductive material, the method comprising:
   providing the enzymatic ink in the hand-held dispenser;
   the substrate comprising the predefined sensor pattern of electrodes; and
   producing a first electrochemical sensor on the substrate by drawing a first active enzyme layer comprising the enzymatic ink on at least one electrode of the predefined sensor pattern of electrodes by using the applicator to apply a first amount of the enzymatic ink dispensed from the squeeze tube onto the at least one electrode of the substrate;
   removing the enzymatic ink from the at least one electrode; and
   producing a second electrochemical sensor on the substrate by drawing a second active enzyme layer comprising the enzymatic ink on the at least one electrode of the predefined sensor pattern of electrodes by using the applicator to apply a second amount of the enzymatic ink dispensed from the squeeze tube onto the at least one electrode of the substrate.

12. The portable enzymatic-ink dispensing system of claim 1, wherein the dispenser is configured as a hand-held stylus.

13. The portable enzymatic-ink dispensing system of claim 1, wherein the substrate is attachable to or integrated with an electronic device operable to implement an electrochemical sensing technique comprising one or more of potentiometry, amperometry, or voltammetry.

14. The portable enzymatic-ink dispensing system of claim 13, wherein electronic device includes a smartphone.

15. The portable enzymatic-ink dispensing system of claim 1, wherein the enzymatic-ink is able to be removable by wiping it off the first electrode of the substrate.

* * * * *